US010392431B2

(12) United States Patent
Vignali et al.

(10) Patent No.: US 10,392,431 B2
(45) Date of Patent: Aug. 27, 2019

(54) POLYNUCLEOTIDE ENCODING IL-35 RECEPTOR

(71) Applicant: St. Jude Children's Research Hospital, Memphis, TN (US)

(72) Inventors: Dario A.A. Vignali, Germantown, TN (US); Lauren Collison, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 21 days.

(21) Appl. No.: 15/430,977

(22) Filed: Feb. 13, 2017

(65) Prior Publication Data

US 2017/0218046 A1 Aug. 3, 2017

Related U.S. Application Data

(62) Division of application No. 13/509,072, filed as application No. PCT/US2010/057369 on Nov. 19, 2010, now abandoned.

(60) Provisional application No. 61/263,058, filed on Nov. 20, 2009.

(51) Int. Cl.

| | |
|---|---|
| ***C12N 15/12*** | (2006.01) |
| ***C07K 14/715*** | (2006.01) |
| ***C07K 16/24*** | (2006.01) |
| ***C12Q 1/6883*** | (2018.01) |
| ***C12Q 1/6886*** | (2018.01) |
| ***C07K 16/28*** | (2006.01) |
| ***G01N 33/50*** | (2006.01) |
| *A61K 39/00* | (2006.01) |

(52) U.S. Cl.

CPC ........ *C07K 14/7155* (2013.01); *C07K 16/244* (2013.01); *C07K 16/2866* (2013.01); *C12Q 1/6883* (2013.01); *C12Q 1/6886* (2013.01); *G01N 33/505* (2013.01); *A01K 2217/05* (2013.01); *A01K 2267/0387* (2013.01); *A61K 2039/505* (2013.01); *C07K 2317/76* (2013.01); *C12Q 2600/158* (2013.01)

(58) Field of Classification Search

CPC .... C07K 14/7155; C12N 15/00; C12N 15/09; C12N 2830/00

See application file for complete search history.

(56) References Cited

U.S. PATENT DOCUMENTS

| | | | |
|---|---|---|---|
| 4,816,567 | A | 3/1989 | Cabilly et al. |
| 5,530,101 | A | 6/1996 | Queen et al. |
| 5,585,089 | A | 12/1996 | Queen et al. |
| 5,693,761 | A | 12/1997 | Queen et al. |
| 5,693,762 | A | 12/1997 | Queen et al. |
| 5,744,301 | A | 4/1998 | Birkenbach et al. |
| 5,750,105 | A | 5/1998 | Newman et al. |
| 5,756,096 | A | 5/1998 | Newman et al. |
| 5,830,451 | A | 11/1998 | Devergne et al. |
| 5,877,397 | A | 3/1999 | Lonberg et al. |
| 5,885,793 | A | 3/1999 | Griffiths et al. |
| 5,939,598 | A | 8/1999 | Kucherlapati et al. |
| 6,075,181 | A | 6/2000 | Kucherlapati et al. |
| 6,091,001 | A | 7/2000 | Jakobovits et al. |
| 6,114,598 | A | 9/2000 | Kucherlapati et al. |
| 6,180,370 | B1 | 1/2001 | Queen et al. |
| 8,784,807 | B2 | 7/2014 | Vignali et al. |
| 9,217,135 | B2 | 12/2015 | Vignali et al. |
| 9,518,113 | B2 | 12/2016 | Vignali et al. |
| 2002/0025317 | A1 | 2/2002 | Leung et al. |
| 2005/0214296 | A1 | 9/2005 | Kastelein et al. |
| 2009/0220498 | A1 | 9/2009 | Finotto |
| 2010/0136019 | A1 | 6/2010 | Vignali et al. |
| 2012/0058096 | A1 | 3/2012 | Vignali et al. |
| 2012/0189578 | A1 | 7/2012 | Collison et al. |

FOREIGN PATENT DOCUMENTS

| | | |
|---|---|---|
| EP | 0572118 | 12/1993 |
| EP | 0759466 | 2/1997 |
| EP | 0 894 854 | 2/1999 |
| WO | WO 94/12519 | 6/1994 |
| WO | WO 97/13859 | 4/1997 |
| WO | WO 01/40257 | 6/2001 |
| WO | WO 2005/016962 | 2/2005 |
| WO | WO 2005/079848 | 9/2005 |
| WO | WO 2005/090400 | 9/2005 |
| WO | WO 2007/045389 | 4/2007 |
| WO | WO 2008/036973 | 3/2008 |
| WO | WO 2008/070097 | 6/2008 |
| WO | WO 2010/101870 | 9/2010 |
| WO | WO 2011/028390 | 3/2011 |
| WO | WO 2011/063198 | 5/2011 |

OTHER PUBLICATIONS

Australian First Examination Report, Australian Application No. 2007298571, dated Sep. 29, 2011, 2 pages.

Bettini, M. et al., "Prevention of Autoimmune Diabetes by Ectopic Pancreatic .beta.-Cell Expression of Interleukin-35," Diabetes, Jun. 2012, pp. 1519-1526, vol. 61.

Canadian First Office Action, Canadian Application No. 2,664,423, dated Dec. 16, 2013, 4 pages.

(Continued)

*Primary Examiner* — Prema M Mertz

(74) *Attorney, Agent, or Firm* — Goodwin Procter LLP

(57) ABSTRACT

The receptor for Interleukin 35 (IL-35) is provided. The Interleukin 35 Receptor (IL-35R) comprises a heterodimeric complex of the Interluekin12Rβ2 receptor and the gp130 receptor. Various compositions comprising the IL-35R complex, along with polynucleotides encoding the same and kits and methods for the detection of the same the same are provided. Methods of modulating the activity of IL-35R or modulating effector T cell functions are also provided. Such methods employ various IL-35R antagonists and agonists that modulate the activity of the IL-35R complex and, in some embodiments, modulate effector T cell function. Further provided are methods for screening for IL-35R binding agents and for IL-35R modulating agents. Various methods of treatment are further provided.

15 Claims, 3 Drawing Sheets

Specification includes a Sequence Listing.

(56) References Cited

OTHER PUBLICATIONS

Canadian Second Office Action, Canadian Application No. 2,664,423, dated Oct. 16, 2014, 3 pages.
Canadian Office Action, Canadian Application No. 2,664,423, dated Oct. 21, 2015, 6 pages.
Collison, L.W. et al., "Interleukin-35: Odd One Out or Part of the Family?" Immunological Reviews, 2008, pp. 248-262, vol. 226.
Collison, L.W. et al., "Interleukin-35-Mediated Induction of a Potent Regulatory T Cell Population," Nature Immunology, Dec. 2010, pp. 1093-1101, vol. 11, No. 12.
Collison L.W. et al., "The Composition and Signaling of the IL-35 Receptor are Unconventional," Nature Immunology, Mar. 2012, pp. 290-299, vol. 13, No. 3.
Collison, L.W. et al., "IL-35-Mediated Induction of a Potent Regulatory T Cell Population," Nature Immunology, 2010, pp. 1-11.
Collison, L.W., et al., "The Inhibitory Cytokine IL-35 Contributes to Regulatory T-Cell Function", Nature, vol. 450, (Nov. 22, 2007), pp. 566-571.
Collison, L.W., "Regulatory T Cell Function is Mediated by the Novel Inhibitory Cytokine Interleukin-35," Revised Version Submitted to Nature Jul. 31, 2007, 37 pages.
Collison, L., "Regulatory T. Cell Supression Is Potentiated by Target T Cells in a Cell Contact, IL-35- and IL-10-Dependent Manner," The Journal of Immunology, 2009, vol. 182(10), pp. 6121-6128.
Devergne, O., et al., "Epstein-Barr Virus-Induced Gene 3 and the p35 Subunit of Interleukin 12 Form a Novel Heterodimeric Hematopoietin", Proc. Natl. Acad. Sci., vol. 94 (Oct. 1997), pp. 12041-12046.
European Application No. 07853605 File History, Retrieved from the European Patent Office Jul. 10, 2015, 385 pages.
Fecci, P.E., "Systemic Anti-CD25 Monoclonal Antibody Administration Safely Enhances Immunity in Murine Glioma without Eliminating Regulatory T Cells," Clinical Cancer Research, Jul. 15, 2006, vol. 12(14), pp. 4294-4305.
Furuichi, Y., et al., "Depletion of CD25+CD4+T cells (Tregs) enhances the HBV-specific CD8+ T cell response primed by DNA immunization," World Journal of Gastroenterology, Jun. 28, 2005, vol. 11(24), pp. 3772-3777.
Maguire Van Seventer, J., et al., "Interferon-.beta. Differentially Regulates Expression of the IL-12 Family Members p35, p40, p19 and EB13 in Activated Human Dendritic Cells", Journal of Neuroimmunology, vol. 133 (2002), pp. 60-71.
Mapara, M.Y., et al., "Tolerance and Cancer: Mechanisms of Tumor Evasion and Strategies for Breaking Tolerance," Journal of Clinical Oncology, Mar. 15, 2004, vol. 22(6), pp. 1136-1151.
Niedbala, W., et al., "IL-35 is a Novel Cytokine with Therapeutic Effects Against Collagen-Induced Arthritis Through the Expansion of Regulatory T Cells and Suppression of Th17 Cells", Eur. J. Immunol., vol. 37, (2007), pp. 3021-3029.
Oppmann, B., et al., "Novel pl9 Protein Engages IL.cndot.l2p40 to Form a Cytokine, IL-23, with Biological Activities Similar as Well as Distinct from IL-12," Immunity, 2000, vol. 13(5), pp. 715-725.
Parham, C., et al., "A Receptor for the Heterodimeric Cytokine IL-23 Is Composed of IL-12RJ31 and a Novel Cytokine Receptor Subunit, IL-23R1," The Journal of Immunology, 2002, vol. 168, pp. 5699-5708.
PCT International Search Report, PCT Application No. PCT/US07/79310, dated Apr. 28, 2008, 7 pages.
PCT Written Opinion, PCT Application No. PCT/US07/79310, dated Apr. 28, 2008, 9 pages.
PCT International Preliminary Examination Report, PCT Application No. PCT/US07/79310, dated Mar. 24, 2009, 10 pages.
PCT International Search Report and Written Opinion, PCT Application No. PCT/US2010/057369, dated Sep. 14, 2011, 18 pages.
Phelan, J., et al., "Cutting Edge: Mechanism of Enhancement of in Vivo Cytokine Effects by Anti-Cytokine Monoclonal Antibodies," The Journal of Immunolou, 2008, vol. 180(1), pp. 44-48.
Pillai , M.R. et al., "The Plasticity of Regulatory T Cell Function," The Journal of Immunology, 2011, pp. 4987-4997, vol. 187.
Waldvogel, A., et al., "Regulation of bovine IL-I 2RJ32 subunit mRNA expression in bovine lymph node cells," Gene, 2002, vol. 289(1-2), pp. 61-67.
Wirtz, S., et al., "EBV-Induced Gene 3 Transcription is Induced by TLR Signaling in Primary Dendritic Cells via NF-.kappa.B Activation", The Journal of Immunology, vol. 174, (2005), pp. 2814-2824.
U.S. Appl. No. 13/389,106, filed Apr. 11, 2012, Inventor Collison, L.W. et al.
United States Office Action, U.S. Appl. No. 12/441,166, dated Nov. 28, 2011, 8 pages.
United States Office Action, U.S. Appl. No. 12/441,166, dated Jun. 7, 2011, 10 pages.
United States Office Action, U.S. Appl. No. 12/441,166, dated Dec. 22, 2010, 11 pages.
United States Office Action, U.S. Appl. No. 14/187,751, dated Jan. 2, 2015, 6 pages.
United States Advisory Action, U.S. Appl. No. 12/441,166, dated Mar. 13, 2012, 3 pages.
United States Office Action, U.S. Appl. No. 13/509,072, dated May 11, 2015, 22 pages.
United States Office Action, U.S. Appl. No. 13/509,072, dated Jan. 6, 2016, 12 pages.
United States Office Action, U.S. Appl. No. 13/509,072, dated Jun. 22, 2016, 15 pages.
United States Office Action, U.S. Appl. No. 14/796,494, dated Apr. 22, 2016, 9 pages.
United States Office Action, U.S. Appl. No. 13/509,072, dated Nov. 14, 2016, 21 pages.
European Boards of Appeal Summons to Appeal Hearing, European Application No. 07853605.9, Mar. 3, 2017, 2 pages.

gp130.fl x CD4.cre x IL12Rb2$^{-/-}$

POLYNUCLEOTIDE ENCODING IL-35 RECEPTOR

CROSS-REFERENCE TO RELATED APPLICATIONS

This application is a Divisional of U.S. application Ser. No. 13/509,072, filed Jul. 27, 2012, which is a U.S. National Stage of International Application No. PCT/US2010/057369, filed Nov. 19, 2010, which designates the U.S and was published by the International Bureau in English on May 26, 2011, and which claims the benefit of U.S. Provisional Application No. 61/263,058, filed Nov. 20, 2009; the contents of each of which are hereby incorporated herein in their entirety by reference, for all purposes.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 36274_US_Sequence_Listings.txt, a creation date of Feb. 9, 2017, and a size of 60.8 KB. The sequence listing filed via EFS-Web is part of the specification and is hereby incorporated in its entirety by reference herein.

FIELD OF THE INVENTION

The present invention relates to methods for regulating T cell function in a subject, particularly effector T cell activity.

BACKGROUND OF THE INVENTION

The immune system provides the human body with a means to recognize and defend itself against microorganisms, viruses, and substances recognized as foreign and potentially harmful. Classical immune responses are initiated when antigen-presenting cells present an antigen to CD4+ T helper (Th) lymphocytes resulting in T cell activation, proliferation, and differentiation of effector T lymphocytes. Following exposure to antigens, such as that which results from infection or the grafting of foreign tissue, naïve T cells differentiate into Th1 and Th2 cells with differing functions. Th1 cells produce interferon gamma (IFN-y) and interleukin 2 (IL-2) (both associated with cell-mediated immune responses). Th1 cells play a role in immune responses commonly involved in the rejection of foreign tissue grafts as well as many autoimmune diseases. Th2 cells produce cytokines such as interleukin-4 (IL-4), and are associated with antibody-mediated immune responses such as those commonly involved in allergies and allergic inflammatory responses such as allergic rhinitis and asthma. Th2 cells may also contribute to the rejection of foreign grafts. In numerous situations, this immune response is desirable, for example, in defending the body against bacterial or viral infection, inhibiting the proliferation of cancerous cells and the like. However, in other situations, such effector T cells are undesirable, e.g., in a graft recipient.

Whether the immune system is activated by or tolerized to an antigen depends upon the balance between T effector cell activation and T regulatory cell activation. T regulatory cells are responsible for the induction and maintenance of immunological tolerance. Regulatory T cells actively suppress the proliferation and cytokine production of Th1, Th2, or nave cells which have been stimulated in culture with an activating signal (e.g., antigen and antigen presenting cells or with a signal that mimics antigen in the context of MEW, e.g., anti-CD3 antibody, plus anti-CD28 antibody).

Undesirable immune responses have generally been treated with immunosuppressive drugs, which inhibit the entire immune system, i.e., both desired and undesired immune responses. General immunosuppressants must be administered frequently, for prolonged periods of time, and have numerous harmful side effects. Withdrawal of these drugs generally results in relapse of disease. Thus, there is a need for agents that preferentially modulate either the effector or the regulatory arm of the immune system.

SUMMARY OF THE INVENTION

The receptor for Interleukin 35 (IL-35) is provided. The Interleukin-35 Receptor (IL-35R) comprises a heterodimeric complex of the Interleukin-12Rβ2 receptor (Il12rb2) and the gp130 receptor (also known as Interleukin-6 signal transducer, Il6st). Various compositions comprising the IL-35R complex, along with polynucleotides encoding the same and kits and methods for the detection of the same are provided.

Methods of modulating the activity of IL-35R or modulating effector T cell functions are provided. Such methods employ various IL-35R antagonists and agonists that modulate the activity of the IL-35R complex and, in some embodiments, modulate effector T cell function. Further provided are methods for screening for IL-35R binding agents and for IL-35R modulating agents. Various methods of treatment are further provided.

DETAILED DESCRIPTION OF THE INVENTION

I. Compositions

Figure 1:
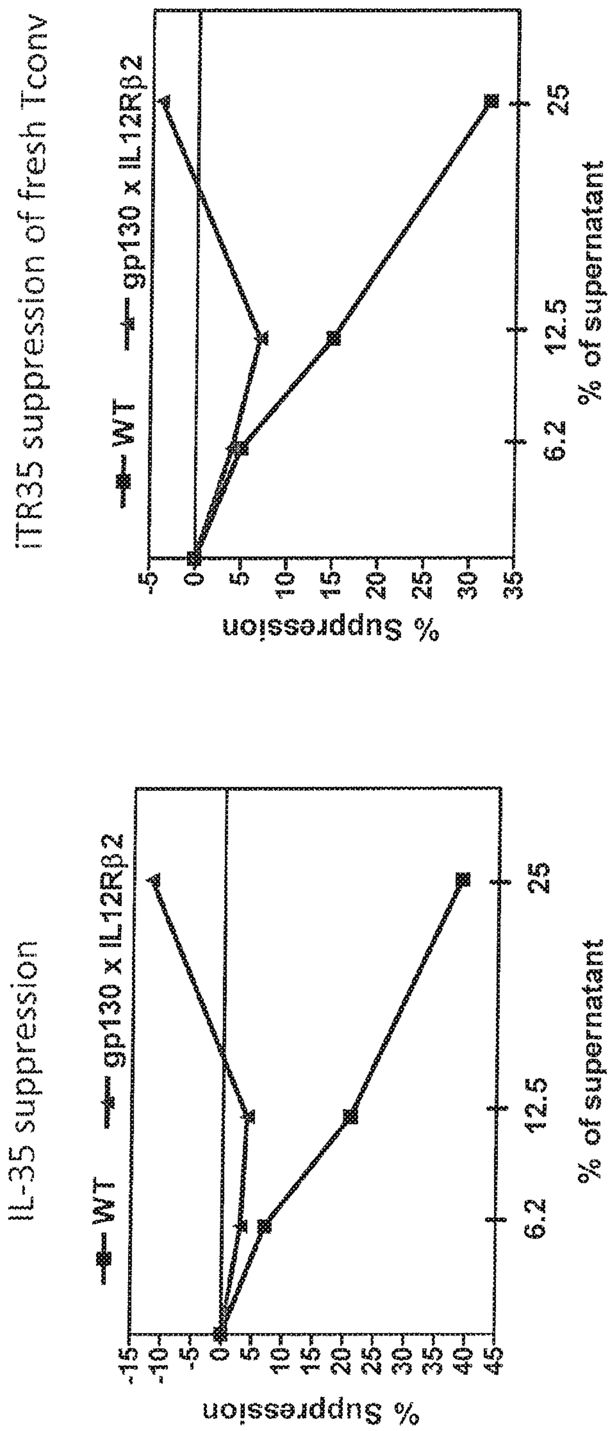
FIG. 1 demonstrates that T-cells that lack both the Interluekin12Rβ2 receptor (IL12Rβ2) and the gp130 receptor are completely resistant to suppression mediated by IL-35 or iTr35, an induced regulatory T cell population that suppresses via IL-35.

The receptor for Interleukin 35 (IL-35) is provided. As demonstrated herein, the Interleukin 35 Receptor (IL-35R) comprises a heterodimeric complex of the Interluekin12Rβ2 receptor (IL12Rβ2) and the gp130 receptor.

As used herein, the Interleukin 35 receptor (IL-35R) refers to any intramolecular complex or single molecule comprising at least one gp130 polypeptide component or biologically active variant or fragment thereof and at least one IL12Rβ2 polypeptide component or biologically active variant or fragment thereof. Typically, in vivo, gp130 and IL12Rβ2 associate via a non-covalent association. For purposes of the present invention, the IL12Rβ2 and gp130 components may be associated with one another either covalently or non-covalently. In some examples, gp130 and IL12Rβ2 can be co-expressed as a fusion protein.

Biologically active fragments and variants of the IL-35R complex are also provided. Such IL-35R complexes comprise an active variant or fragment of gp130 and/or an active variant or fragment of IL12Rβ2 and will retain at least one activity of the IL-35R complex.

The phrase "biological activity of IL-35R" refers to one or more of the biological activities of IL-35R, including but not limited to, (1) interacting with its ligand, IL-35; (2) activating any of the STAT pathways including the STAT1 and/or STAT4 pathways; (3) IL-35 dependent suppression of effector T-cell function, including for example, suppression of proliferation, cytokine secretion and/or differentiation; and/or (4) autocrine induction of IL-35 expression by IL-35. Such assays can be found, for example, in Collison et al. (2007) Nature 450:566-569; Collison et al. (2010) Nature Immunology 11: 1093-1101.

As discussed above, the IL-35R complex interacts with the ligand, IL-35. As used herein, "Interleukin 35" or "IL-35" refers to any intramolecular complex or single molecule comprising at least one EBI3 polypeptide component and at least one p35 polypeptide component. See, for example, International Patent Application No. PCT/US2007/079310, filed Sep. 24, 2007, herein incorporated by reference in its entirety. EBI3 and p35 are known in the art. The human EBI3 gene encodes a protein of about 33 kDa. The protein shares about 27% sequence identity to the p40 subunit of human IL12. Nucleic acid and amino acid sequences for EBI3 are known. See, for example, SEQ ID NOs:1 and 2 of WO97/13859 (human) and GenBank Accession Numbers NM015766 and BC046112 (mouse). Nucleic acid and amino acid sequences for p35 are also known in the art and include SEQ ID NOs:3 and 4 of WO97/13859 (human) and GenBank Accession Numbers NM_000882 and M86672 (mouse). The term IL-35 encompasses naturally occurring variants of IL-35, e.g., splice variants, allelic variants, and other isoforms. The term also encompasses fragments or variants of a native IL-35 such that the active variants and fragment continue to bind and allow for the activation of IL-35R.

It is recognized that an IL-35R complex can be encoded on a single polynucleotide. For example, in one embodiment, a polynucleotide comprising a nucleotide sequence encoding an Interleukin 35 receptor (IL-35R) complex is provided and comprises a first sequence encoding the gp130 polypeptide or an active fragment or variant thereof; and a second sequence encoding the IL12Rβ2 polypeptide or an active fragment or variant thereof, wherein said encoded polypeptides form a biologically active IL-35R complex. In another embodiment, the IL-35R complex is encoded on distinct polynucleotides. Thus, a mixture of recombinant expression constructs encoding the various components of the IL-35R complex are further provided.

i. IL12Rβ2 Polynucleotides and Polypeptides

The polypeptides that interact to form the IL-35R complex are known in the art. As used herein, the terms "Interleukin12Rβ2 receptor", "IL12Rβ2" or "IL-12R-beta2" can be used interchangeably and refer to a family of cell surface receptors which can homodimerize or heterodimerize and display interleukin receptor activity and have now been shown herein to be a subunit of the IL-35R complex. Non-limiting examples of IL12Rβ2 polypeptides comprise the human IL12Rβ2 polynucleotide as set forth in SEQ ID NO:4, 5, and 6 (from GenBank Accession No. NM_001559.2) and can be found in GenBank Accession No. P40189.

IL12Rβ2 polypeptides comprise a variety of conserved structural motifs. For ease of reference, such motifs will be discussed as they relate to the human IL12Rβ2 isoform 1 which is set forth in SEQ ID NO:6. IL12Rβ2 polypeptides comprise an extracellular domain (from about amino acids 24-522 of SEQ ID NO:6); a transmembrane domain (from about amino acids 623-643 of SEQ ID NO:3), and an intercellular domain (from about amino acids 644-862 of SEQ ID NO:6). Additional conserved domains and motifs that have been characterized in the IL12Rβ2 polypeptides include a signal peptide (from about amino acids 1-23 of SEQ ID NO:6), a Fibronectin type III I domain (from about amino acids 124-218 of SEQ ID NO:6), a Fibronectin type III 2 domain (from about amino acids 224-316 of SEQ ID NO:6), a Fibronectin type III 3 domain (from about amino acids 317-415 of SEQ ID NO:6), a Fibronectin type III 4 domain (from about amino acids 420-517 of SEQ ID NO:6), a Fibronectin type III 5 domain (from about amino acids 521-617 of SEQ ID NO:6), a motif involved with STAT4 binding (from about amino acids 796-801 of SEQ ID NO:6), a WSXWS motif (from about amino acids 305-309 of SEQ ID NO:6) which appears to be involved in proper protein folding and thereby efficient intracellular transport and cell-surface receptor binding, and a Box 1 motif (from about amino acids 662-670 of SEQ ID NO:6) which is involved in JAK interaction and/or activation. Glycosylation can occur at amino acid positions 48, 129, 166, 195, 271, 347, 376, and 480 of SEQ ID NO:6.

It is recognized that biologically active variants and fragments of the IL12Rβ2 polypeptide can be employed in the various methods and compositions of the invention. Such active variants and fragments will contain an IL-35R receptor activity when complexed with the gp130 partner. Variants of IL12Rβ2 are known including, but not limited to, an alternative sequence from aa 650-659 of SEQ ID NO:6 replacing VFVLLAALRP with RRHSCPWTGS; an alternative sequence from aa 660-862 of SEQ ID NO:6 is missing; the R at aa 149 of SEQ ID NO:6 is replaced with Q; the I at aa 185 of SEQ ID NO:6 is replaced with V; the T at aa 201 of SEQ ID NO:6 is replaced with I; the R at aa 313 of SEQ ID NO:6 is replaced with G; the G at aa 420 of SEQ ID NO:6 is replaced with R; the Q at aa 426 of SEQ ID NO:6 is replaced with H; the G at aa 465 of SEQ ID NO:6 is replaced with D; the A at aa 625 of SEQ ID NO:6 is replaced with V; the H at aa 720 of SEQ ID NO:6 is replaced with R; the L at aa 808 of SEQ ID NO:6 is replaced with R; the Y at aa 678 of SEQ ID NO:6 is replaced with F; or the Y at aa 767 of SEQ ID NO:6 is replaced with F.

In specific embodiments, fragments of IL12Rβ2 are employed which comprise the extracellular domain of the IL12Rβ2 polypeptide or a biologically active fragment or variant of the extracellular domain of IL12Rβ2. Such biologically active variants and fragments of the IL12Rβ2 extracellular domain will retain the ability to complex with the gp130 binding partner's extracellular domain and upon complex formation, the gp130/IL12Rβ2 complex will interact with the IL-35 ligand. Methods to assay for such binding are known.

Thus, in one embodiment, the IL12Rβ2 polypeptide comprises the amino acid sequence as shown in SEQ ID NO:6 or a biologically active variant or fragment thereof. Further provided are polynucleotides comprising the nucleotide sequence encoding a IL12Rβ2 polypeptide including the nucleotide sequence set forth in SEQ ID NO:4 or 5 or a biologically active variant or fragment thereof.

ii. Gp130 Polynucleotides and Polypeptides

As used herein, the terms "gp130", "Interleukin-6-receptor subunit beta", "IL-6R-beta", "Interleukin-6-signal transducer", "membrane glycoprotein 130", "CDW130", "Oncostatin-M receptor alpha subunit", "CD_antigen=CD130" or IL6ST" can be used interchangeably and refer to a family of cell surface receptors which can homodimerize or heterodimerize and display interleukin receptor activity and have now been shown herein to be a subunit of the IL-35R complex. Non-limiting examples of gp130 polypeptides comprising the human gp130 polynucleotide and polypeptide are set forth in SEQ ID NOs: 1, 2, and 3 (GenBank Accession No. NP_002184.2) or also in GenBank Accession No. P40189.

The gp130 polypeptide comprises a variety of conserved structural motifs and belongs to the type I cytokine receptor family. For ease of reference, such motifs will be discussed as they relate to the human gp130 isoform 1 which is set forth in SEQ ID NO:3. gp130 polypeptides comprise an extracellular domain (from about amino acids 23-619 of SEQ ID NO:3); a transmembrane domain (from about amino acids 260-641 of SEQ ID NO:3), and an intercellular domain (from about amino acids 642-918 of SEQ ID NO:3). Additional conserved domains and motifs have been characterized in the gp130 polypeptides include a signal peptide (from about amino acids 1-22 of SEQ ID NO:3), an IG-like C2-type domain (from about amino acids 26-120 of SEQ ID NO:3), a Fibronectin type III I domain (from about amino acids 125-216 of SEQ ID NO:3), a Fibronectin type III 2 domain (from about amino acids 222-321 of SEQ ID NO:3), a Fibronectin type III 3 domain (from about amino acids 326-418 of SEQ ID NO:3), a Fibronectin type III 4 domain (from about amino acids 423-514 of SEQ ID NO:3), a Fibronectin type III 5 domain (from about amino acids 518-610 of SEQ ID NO:3), a WSXWS motif (from about amino acids 310-314 of SEQ ID NO:3) which appears to be involved in proper protein folding and thereby efficient intracellular transport and cell-surface receptor binding, a Box 1 motif (from about amino acids 651-659 of SEQ ID NO:3) which is involved in JAK interaction and/or activation, and a compositional bias that is Ser-rich (from about amino acids 725-755 of SEQ ID NO:3). Glycosylation can occur at amino acid positions 43, 83, 131, 157, 227, 379, 383, 553, 564 of SEQ ID NO:3. Modified phosphoserine residues can occur at amino acids 667, 782, 820, and 829 of SEQ ID NO:3. Disulfide bonds can occur between amino acids 28 and 54, 48 and 103, 134 and 144, 172 and 182, and 458 and 466 of SEQ ID NO:3.

It is recognized that biologically active variants and fragments of the gp130 polypeptide can be employed in the various methods and compositions of the invention. Such active variants and fragments will continue to retain an IL-35R activity when complexed with the IL12Rβ2 partner. Variants and fragments of gp130 polypeptides and polynucleotides are known including, but not limited to, an alternative sequence from aa 325-329 of SEQ ID NO:3 replacing RPSKA with NIASF; an alternative sequence from aa 330-918 of SEQ ID NO:3 is missing; the Tat aa 415 of SEQ ID NO:3 is replaced with I; or the S at aa 782 of SEQ ID NO:3 is replaced with A.

In specific embodiments, fragments of the gp130 are employed which comprise the extracellular domain of the gp130 polypeptide or a biologically active fragment or variant of the extracellular domain of gp130. Such biologically active variants and fragments of the extracellular domain of gp130 will retain the ability to complex with the IL12Rβ2 binding partner's extracellular domain and upon complex formation, the gp130/IL12Rβ2 complex can interact with the IL-35 ligand. Methods to assay for such binding are known.

Thus, in one embodiment, the gp130 polypeptide comprises the amino acid sequence as shown in SEQ ID NO:3 or a biologically active variant or fragment thereof. Further provided are polynucleotides comprising the nucleotide sequence encoding a gp130 polypeptide including the nucleotide sequence set forth in SEQ ID NO:1 or 2 or a biologically active variant or fragment thereof.

iii. Variants and Fragments

Fragments and variants of the polynucleotides encoding the gp130 and IL12Rβ2 polypeptides can be employed in the various methods and compositions of the invention. By "fragment" is intended a portion of the polynucleotide and hence the protein encoded thereby or a portion of the polypeptide. Fragments of a polynucleotide may encode protein fragments that retain the biological activity of the native protein and hence have IL-35R activity when complexed with the appropriate binding partner. Thus, fragments of a polynucleotide may range from at least about 20 nucleotides, about 50 nucleotides, about 100 nucleotides, about 150, about 200, about 250, about 300, about 350, about 400, about 450, about 500, about 550, about 600 and up to the full-length polynucleotide encoding the gp130 or IL12Rβ2 polypeptide.

A fragment of a polynucleotide that encodes a biologically active portion of a gp130 or IL12Rβ2 polypeptide will encode at least 15, 25, 30, 50, 100, 150, 200, or 250 contiguous amino acids, or up to the total number of amino acids present in a full-length gp130 and IL12Rβ2 polypeptide.

A biologically active portion of a gp130 or IL12Rβ2 polypeptide can be prepared by isolating a portion of one of the polynucleotides encoding the portion of the gp130 or IL12Rβ2 polypeptide and expressing the encoded portion of the polypeptide (e.g., by recombinant expression in vitro), and assessing the activity of the portion of the gp130 or IL12Rβ2 polypeptide. Polynucleotides that encode fragments of a gp130 or IL12Rβ2 polypeptide can comprise nucleotide sequence comprising at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length gp130 and IL12Rβ2 nucleotide sequence disclosed herein.

"Variant" sequences have a high degree of sequence similarity. For polynucleotides, conservative variants include those sequences that, because of the degeneracy of the genetic code, encode the amino acid sequence of one of the gp130 or IL12Rβ2 polypeptides. Variants such as these can be identified with the use of well-known molecular biology techniques, as, for example, polymerase chain reaction (PCR) and hybridization techniques. Variant polynucleotides also include synthetically derived nucleotide sequences, such as those generated, for example, by using site-directed mutagenesis but which still encode a gp130 or a IL12Rβ2 polypeptide. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the gp130 and IL12Rβ2 polypeptides set forth herein. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins are biologically active, that is they continue to possess the desired biological activity of the native protein, that is, IL-35R activity. Such variants may result from, for example, genetic polymorphism or from human manipulation. Biologically active variants of a gp130 or IL12Rβ2 polypeptides will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein may differ from that protein by as few as 1-15 amino acid residues, as few as 1-10, such as 6-10, as few as 5, as few as 4, 3, 2, or even 1 amino acid residue.

Proteins may be altered in various ways including amino acid substitutions, deletions, truncations, and insertions. Methods for such manipulations are generally known in the art. For example, amino acid sequence variants of the gp130 or IL12Rβ2 proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the polynucleotides used in the invention can include the naturally occurring sequences, the "native" sequences, as well as mutant forms. Likewise, the proteins used in the methods of the invention encompass naturally occurring proteins as well as variations and modified forms thereof. Such variants will continue to possess the ability to implement a recombination event. Generally, the mutations made in the polynucleotide encoding the variant polypeptide should not place the sequence out of reading frame, and/or create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant polynucleotides and proteins also encompass sequences and proteins derived from a mutagenic and recombinogenic procedure such as DNA shuffling. With such a procedure, one or more different gp130 or IL12Rβ2 coding sequences can be manipulated to create a new gp130 or IL12Rβ2 polypeptides possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

iv. IL-35R Binding and/or Modulating Agents

1. Modulating Agents

As used herein, the term "modulating" includes "inducing", "inhibiting", "potentiating", "elevating", "increasing", "decreasing" or the like. Each of these terms denote a quantitative difference between two states and in particular, refer to at least a statistically significant difference between the two states.

The term "IL-35R agonist" refers to an agent which potentiates, induces or otherwise enhances one or more of the biological properties of the IL-35R complex. The activity increases by a statistically significant amount including, for example, an increase of at least about 5%, 10%, 15%, 20%, 25%, 30%, 35%, 40%, 45%, 50%, 55%, 60%, 65%, 70%, 75%, 80%, 85%, 95% or 100% of the activity of the IL-35R complex compared to an appropriate control.

The term "IL-35R antagonist" refers to an agent which reduces, inhibits, or otherwise diminishes one or more of the biological activities of the IL-35R complex. Antagonism using the IL-35R antagonist does not necessarily indicate a total elimination of the IL-35R activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of the IL-35R complex compared to an appropriate control.

By "specific modulating agent" is intended an agent that modulates the activity of a defined target. Thus, an IL-35R specific modulating agent modulates the biological activity of IL-35R by a statically significant amount (i.e., at least 5%, 10%, 20%, 30%, 40%, 50%, 60%, 70%, 80%, 90%, 100% or greater) and the agent does not modulate the biological activity of any monomeric subunits, homodimeric complexes or non-IL-35R heterodimeric complexes which comprise either IL12Rβ2 or gp130 by a statistically significant amount (i.e., the activity is modulated by less than 5%, 4%, 3%, 2% or 1%). One of skill will be aware of the proper controls that are needed to carry out such a determination. An IL-35R specific modulating agent may or may not be an IL-35R specific binding agent.

In one non-limiting embodiment, the IL-35R modulating agent comprises a soluble IL-35R complex. Such a soluble complex is an IL-35R. As used herein, a "soluble IL-35R complex" comprises an IL-35R polypeptide that is incapable of anchoring itself in a membrane. Such soluble IL-35R polypeptides include, for example, a complex of gp130 and/or IL12Rβ2 polypeptides that lack a sufficient portion of their membrane spanning domain to anchor the IL-35R to the membrane or such polypeptides are modified such that the membrane spanning domain is non-functional. For example, a soluble fragment of a gp130 polypeptide comprises the extracellular domain of gp130, including a fragment of the extracellular domain that is at least 20, 30, 40, 50, 60, 70, 90, 100, 150, 200, 250, 300, 350, 400, 450, 500, 550, 590 or greater consecutive amino acids of gp130. A soluble fragment of an IL12Rβ2 polypeptide comprises the extracellular domain of IL12Rβ2, including a fragment of the extracellular domain that is at least 20, 30, 40, 50, 60, 70, 90, 100, 150, 200, 250, 300, 350, 400, 450, 495 or greater consecutive amino acids of IL12Rβ2. In specific embodiments, the soluble IL-35R complex binds IL-35. In other embodiments, the extracellular domains of gp130 and IL12Rβ2 that are present in the soluble form of the IL-35R complex share at least 70%, 75%, 80%, 85%, 90%, 91%, 92%, 93%, 94%, 95%, 96%, 97%, 98%, 99% to the amino acid sequence or the polynucleotide sequences as set forth in SEQ ID NO: 1, 2, 3, 4, 5 or 6. The soluble IL-35R complex find further use in stabilizing IL-35 (increasing half-life) or acting to concentrate IL-35.

A soluble IL-35R complex can additionally include a second moiety. The second moiety can be any chemical compound. In specific embodiments, the second moiety adds in the detection of the soluble complex or promotes the overall solubility of the complex. Such moieties include, but are not limited to, an immunoglobulin chain, a GST, Lex-A or MBP polypeptide sequence. For example, a fusion protein can includes at least a fragment of an IL-35R complex, which is capable of binding IL-35, wherein the IL-35R complex comprises a soluble fragment of a gp130 (e.g., a fragment of gp130 comprising the extracellular domain of gp130) and a soluble fragment of IL12Rβ2 (e.g., a fragment of IL12Rβ2 comprising the extracellular domain of IL12Rβ2) wherein at least one of the gp130 fragment, the IL12Rβ2 fragment, or both are fused to a second moiety. In specific embodiments, the second moiety comprises an immunoglobulin chain, an Fc fragment ($CH_2$, hinge, $CH_3$ constant region domains), a heavy chain constant region domain of the various isotypes, including: IgG1, IgG2, IgG3, IgG4, IgM, IgA1, IgA2, IgD, and IgE).

A soluble form of the IL-35R complex can be generated using various protein motifs that assist in complex formation. One such motif comprises a leucine zipper motif. Leucine zipper domains are peptides that promote oligomerization of the polypeptides in which they are found. Leucine zippers were originally identified in several DNA-binding polypeptides (Landschulz et al. (1988) *Science* 240:1759), and have since been found in a variety of different polypeptides. Among the known leucine zippers are naturally occurring peptides and derivatives thereof that dimerize or trimerize. The zipper domain (also referred to herein as an oligomerizing, or oligomer-forming, domain) comprises a repetitive heptad repeat, often with four or five leucine residues interspersed with other amino acids. Use of leucine zippers and preparation of oligomers using leucine zippers are well known in the art. Any other method which assists in the stabilization of the soluble complex can be employed.

It is recognized that a soluble IL-35R complex can be encoded on a single polynucleotide. For example, in one embodiment, a polynucleotide comprising a nucleotide sequence encoding a soluble Interleukin 35 receptor (IL-35R) complex is provides and comprise a first sequence encoding the extracellular domain of gp130, an active fragment or variant thereof; and a second sequence encoding the extracellular domain of IL12Rβ2, active fragment or variant thereof, the encoded soluble polypeptide complex bind IL-35. In another embodiment, the soluble IL-35R complex is encoded on distinct polynucleotides.

In another embodiment, a "specific modulating agent" can comprise an agent, such as an antibody, which modulates the ability of the IL-35R to be activated by IL-35 but permits the IL-35R complex to be activated by other non-IL-35 ligands. Such agents can be IL-35R binding agents, a gp130 binding agent, or an IL12Rβ2 binding agent.

2. IL-35R Binding Agents

As used herein, an "IL-35R binding agent" refers to any compound that directly interacts with or binds to the IL-35R complex. By "specific binding agent" is intended an agent that binds substantially only to a defined target. Thus, an IL-35R specific binding agent interacts directly with IL-35R and binds substantially only to epitopes which are formed upon the interaction of IL12Rβ2 and gp130 to form the biologically active IL-35R. Thus, an IL-35R specific binding agent will not substantially interact with monomeric protein subunits comprising IL12Rβ2 or gp130 and the agent will not substantially interact with homodimeric or non-IL-35R heterodimeric complexes which comprise IL12Rβ2 or gp130 in a statistically significant amount. By "specifically or selectively binds to an IL-35R complex" is intended that the binding agent has a binding affinity for a non-IL-35R epitope which is less than 10%, 9%, 8%, 7%, 6%, 5%, 4%, 3%, 2% or 1% of the binding affinity for the unique IL-35R epitope. One of skill will be aware of the proper controls that are needed to carry out such a determination. An IL-35R specific binding agent may or may not modulate the activity of IL-35R.

By "IL-35R specific binding/modulating agent" is intended an agent that possesses the properties of both an IL-35R specific binding agent and an IL-35R specific modulating agent. The IL-35R specific binding and/or modulating agent can be an IL-35R agonist or an IL-35R antagonist.

By "IL-35 activation" is intended any activity resulting from the binding of IL-35 to the IL-35R complex. As used herein, an agent that "specifically inhibits" IL-35 activity of the IL-35R complex will substantially block the activity of IL-35R by IL-35, but will not significantly block the activity of IL-35R by a non-IL-35 ligand.

In one embodiment, the IL-35R binding and/or modulating agent is a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heterorganic and organometallic compounds).

3. Anti-IL-35R Antibodies

As noted herein, the invention includes antibodies that specifically bind to the IL-35R complex. Antibodies, including monoclonal antibodies (mAbs), can be made by standard protocols. See, for example, Harlow and Lane, *Using Antibodies: A Laboratory Manual*, CSHL, New York, 1999. Briefly, a mammal such as a mouse, hamster or rabbit can be immunized with an immunogenic form of a peptide. Techniques for conferring immunogenicity on a protein or peptide include conjugation to carriers or other techniques, well known in the art. In preferred embodiments, the subject antibodies are immunospecific for the unique antigenic determinants of IL-35R.

As discussed herein, these antibodies are collectively referred to as "anti-IL-35R antibodies". Thus, by "anti-IL-35R antibodies" is intended antibodies specific for IL-35R. All of these antibodies are encompassed by the discussion herein. The respective antibodies can be used alone or in combination in the methods of the invention.

By "antibodies that specifically bind" is intended that the antibodies will not substantially cross react with another polypeptide. By "not substantially cross react" is intended that the antibody or fragment has a binding affinity for a non-homologous protein which is less than 10%, less than 5%, or less than 1%, of the binding affinity for the IL-35R complex.

In specific embodiments, the anti-IL-35R antibody binds specifically to IL-35R and further modulates the activity of the IL-35R complex. Thus, in specific embodiments, the anti-IL-35R antibody is an IL-35R agonist or is an IL-35R antagonist.

The anti-IL-35R antibodies disclosed herein and for use in the methods of the present invention can be produced using any antibody production method known to those of skill in the art. Thus, polyclonal sera may be prepared by conventional methods. In general, a solution containing the IL-35R complex or an active variant or fragment thereof is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies.

Polyclonal sera can be prepared in a transgenic animal, preferably a mouse bearing human immunoglobulin loci. In a preferred embodiment, Sf9 (*Spodoptera frugiperda*) cells expressing IL-35R are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Production of the Sf9 cells is disclosed in U.S. Pat. No. 6,004,552. Briefly, sequences encoding IL-35R complex are recombined into a baculovirus using transfer vectors. The plasmids are co-transfected with wild-type baculovirus DNA into Sf9 cells. Recombinant baculovirus-infected Sf9 cells are identified and clonally purified.

Preferably the antibody is monoclonal in nature. By "monoclonal antibody" is an antibody obtained from a population of substantially homogeneous antibodies, that is, the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site on the target polypeptide. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein (*Nature* 256:495-97, 1975), or may be made by recombinant DNA methods (see, e.g., U.S. Pat. No. 4,816,567). The "monoclonal antibodies" may also be isolated from phage antibody libraries using the techniques described in, for example, Clackson et al. (*Nature* 352:624-28, 1991), Marks et al. (*J. Mol. Biol.* 222:581-97, 1991) and U.S. Pat. No. 5,514,548.

By "epitope" is the part of an antigenic molecule to which an antibody is produced and to which the antibody will bind. Epitopes can comprise linear amino acid residues (i.e., residues within the epitope are arranged sequentially one after another in a linear fashion), nonlinear amino acid residues (referred to herein as "nonlinear epitopes"—these epitopes are not arranged sequentially), or both linear and nonlinear amino acid residues.

As discussed herein, mAbs can be prepared using the method of Kohler and Milstein, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected mAb-secreting hybridomas are then cultured either in vitro (e.g., in tissue culture bottles or hollow fiber reactors), or in vivo (as ascites in mice).

Where the anti-IL-35R antibodies of the invention are to be prepared using recombinant DNA methods, the DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA can be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding an antibody includes Skerra, A. (*Curr. Opinion in Immunol.* 5:256-62, 1993) and Phickthun, A. (*Immunol. Revs.* 130:151-88, 1992). Alternatively, antibody can be produced in a cell line such as a CHO cell line, as disclosed in U.S. Pat. Nos. 5,545,403; 5,545,405 and 5,998,144. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

Additionally, the term "anti-IL-35R antibody" as used herein encompasses chimeric and humanized anti-IL-35R antibodies. By "chimeric" antibodies is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the IL-35R antigen. The non-human source can be any vertebrate source that can be used to generate antibodies to a human IL-35R antigen or material comprising a human IL-35R antigen. Such non-human sources include, but are not limited to, rodents (e.g., rabbit, rat, mouse, etc.; see, e.g., U.S. Pat. No. 4,816,567) and non-human primates (e.g., Old World Monkeys, Apes, etc.; see, e.g., U.S. Pat. Nos. 5,750,105 and 5,756,096). As used herein, the phrase "immunologically active" when used in reference to chimeric/humanized anti-IL-35R antibodies means chimeric/humanized antibodies that bind human IL-35R.

By "humanized" is intended forms of anti-IL-35R antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. The phrase "complementarity determining region" refers to amino acid sequences which together define the binding affinity and specificity of the natural FAT region of a native immunoglobulin binding site. See, for example, Chothia et al. (*J. Mol. Biol.* 196:901-17, 1987) and Kabat et al. (U. S. Dept. of Health and Human Services, NIH Publication No. 91-3242, 1991). The phrase "constant region" refers to the portion of the antibody molecule that confers effector functions.

Humanization can be essentially performed following the methods described by Jones et al. (*Nature* 321:522-25, 1986), Riechmann et al. (*Nature* 332:323-27, 1988) and Verhoeyen et al. (*Science* 239:1534-36, 1988), by substituting rodent or mutant rodent CDRs or CDR sequences for the corresponding sequences of a human antibody. See also U.S. Pat. Nos. 5,225,539; 5,585,089; 5,693,761; 5,693,762; and 5,859,205. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. Accordingly, such "humanized" antibodies may include antibodies wherein substantially less than an intact human variable domain has been substituted by the corresponding sequence from a non-human species.

Also encompassed by the term "anti-IL-35R antibodies" are xenogeneic or modified anti-IL-35R antibodies produced in a non-human mammalian host, more particularly a transgenic mouse, characterized by inactivated endogenous immunoglobulin loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598. Preferably, fully human antibodies to IL-35 can be obtained by immunizing transgenic mice. One such mouse is disclosed in U.S. Pat. Nos. 6,075,181; 6,091,001; and 6,114,598.

Fragments of the anti-IL-35R antibodies are suitable for use in the methods of the invention so long as they retain the desired affinity of the full-length antibody. Thus, a fragment of an anti-IL-35R antibody will retain the ability to specifically bind to IL-35R. Such fragments are characterized by properties similar to the corresponding full-length anti-IL-35R antibody; that is, the fragments will specifically bind IL-35R. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, $F(ab')_2$, and Fv fragments and single-chain antibody molecules. By "Fab" is intended a monovalent antigen-binding fragment of an immunoglobulin that is composed of the light chain and part of the heavy chain. By $F(ab')_2$ is intended a bivalent antigen-binding fragment of an immunoglobulin that contains both light chains and part of both heavy chains.

By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778; 5,260,203; 5,455,030; and 5,856,456. Generally, the Fv polypeptide further comprises a polypeptide linker between the $V_H$ and $V_L$ domains that enables the sFv to form the desired structure for antigen binding. For a review of sFv see Pluckthun, A. (1994) in *The Pharmacology of Monoclonal Antibodies*, Vol. 113, ed. Rosenburg and Moore (Springer-Verlag, New York), pp. 269-315.

Antibodies or antibody fragments can be isolated from antibody phage libraries generated using the techniques described in, for example, McCafferty et al. (*Nature* 348:552-54, 1990) and U.S. Pat. No. 5,514,548. Clackson et al. (*Nature* 352:624-28, 1991) and Marks et al. (*J. Mol. Biol.* 222:581-97, 1991) describe the isolation of murine and human antibodies, respectively, using phage libraries. Subsequent publications describe the production of high affinity (nM range) human antibodies by chain shuffling (Marks et al., *Bio/Technology* 10:779-83, 1992), as well as combinatorial infection and in vivo recombination as a strategy for constructing very large phage libraries (Waterhouse et al., *Nucleic. Acids Res.* 21:2265-66, 1993). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al., *J. Biochem. Biophys. Methods* 24:107-17, 1992 and Brennan et al., *Science* 229:81-3, 1985). However, these fragments can now be produced directly by recombinant host cells. For example, the antibody fragments can be isolated from the antibody phage libraries discussed above. Alternatively, Fab fragments can be directly recovered from *E. coli* and chemically coupled to form $F(ab')_2$ fragments (Carter et al., *Bio/Technology* 10:163-67, 1992). According to another approach, $F(ab')_2$ fragments can be isolated directly from recombinant host cell culture. Other techniques for the production of antibody fragments will be apparent to the skilled practitioner.

A representative assay to detect anti-IL-35R antibodies specific to the unique epitopes form upon complex formation of IL-35R is a "competitive binding assay." Competitive binding assays are serological assays in which unknowns are detected and quantitated by their ability to inhibit the binding of a labeled known ligand to its specific antibody. Antibodies employed in such immunoassays may be labeled or unlabeled. Unlabeled antibodies may be employed in agglutination; labeled antibodies may be employed in a wide variety of assays, employing a wide variety of labels. Detection of the formation of an antibody-antigen complex between an anti-IL-35R antibody and an epitope of interest can be facilitated by attaching a detectable substance to the antibody. Suitable detection means include the use of labels such as radionucleotides, enzymes, coenzymes, fluorescers, chemiluminescers, chromogens, enzyme substrates or co-factors, enzyme inhibitors, prosthetic group complexes, free radicals, particles, dyes, and the like. Such labeled reagents may be used in a variety of well-known assays, such as radioimmunoassays, enzyme immunoassays, e.g., ELISA, fluorescent immunoassays, and the like. See, for example, U.S. Pat. Nos. 3,766,162; 3,791,932; 3,817,837; and 4,233,402.

In still further embodiments, the antibody is bispecific, wherein a first antigen binding domain specifically interacts with an epitope of gp130 and said second antigen binding domain specifically interacts with an epitope of IL12Rβ2.

Further provided is a mixture of a first and a second antibody. The mixture comprise a first antibody having a first chemical moiety and the first antibody binds substantially only to gp130 and a second antibody having a second chemical moiety and the second antibody bind substantially only to a second polypeptide comprising IL12Rβ2. The first and the second chemical moiety allow for the interaction of said first and said second antibody at an IL-35R complex to be detected. Methods for such forms of detection and chemical moieties of interest are discussed elsewhere herein.

4. Anti-gp130 and Anti-IL12Rβ2 Antibodies

The compositions further include antibodies that specifically bind to the constituents of the IL-35R complex: gp130 and IL12Rβ2. As described above, techniques for conferring immunogenicity on a protein or peptide include conjugation to carriers or other techniques, well known in the art. In preferred embodiments, anti-gp130 and anti-IL12Rβ2 antibodies are immunospecific for the unique antigenic determinants of gp130 and IL12Rβ2, respectively. The term "anti-gp130 antibody" as used herein encompasses an antibody that binds substantially only to a gp130 polypeptide or a biologically active variant or fragment thereof, where the antibody behaves as a specific modulating agent for IL-35R and substantially inhibits IL-35 activation of the IL-35R complex. The term "anti-IL12Rβ2 antibody" as used herein encompasses an antibody that binds substantially only to an IL12Rβ2 polypeptide or a biologically active variant or fragment thereof, where such an antibody behaves as a specific modulating agent for IL-35R and substantially inhibits IL-35 activation of the IL-35R complex. In some embodiments, anti-gp130 and anti-IL12Rβ2 antibodies can be "specific modulating agents" which modulate the ability of the IL-35R to be activated by IL-35 but permit the IL-35R complex to be activated by other non-IL-35 ligands. Thus, in some embodiments, an anti-gp130 antibody can bind substantially only to a gp130 polypeptide, or a biologically active variant or fragment thereof, and act as a specific modulating agent for IL-35R by substantially and specifically inhibiting IL-35 activation of the IL-35R complex. In such cases, IL-35R activation by non-IL-35 ligands can include, for example, the binding of Interleukin 27 (IL-27) or Interleukin 12 (IL-12) to the IL-35R complex. Methodologies provided herein for the production and use of anti-IL-35R antibodies can be adapted to make and use anti-gp130 and anti-IL12Rβ2 antibodies.

vi. Expression Cassettes and Host Cells

The various polynucleotides of the invention can be expressed in an expression cassette. An expression cassette comprises one or more regulatory sequences, selected on the basis of the cells to be used for expression, operably linked to the desired polynucleotide. "Operably linked" is intended to mean that the desired polynucleotide (i.e., gp130 and/or IL12Rβ2 or active variants and fragments thereof) is linked to the regulatory sequence(s) in a manner that allows for expression of the nucleotide sequence (e.g., in an in vitro transcription/translation system or in a cell when the expression cassette or vector is introduced into a cell). "Regulatory sequences" include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cells, those that direct expression of the nucleotide sequence only in certain host cells (e.g., tissue-specific regulatory sequences), or those that direct expression of the polynucleotide in the presence of an appropriate inducer (inducible promoter). It will be appreciated by those skilled in the art that the design of the expression cassette can depend on such factors as the choice of the host cell to be transformed, the level of expression of the polynucleotide that is desired, and the like. Such expression cassettes typically include one or more appropriately positioned sites for restriction enzymes, to facilitate introduction of the nucleic acid into a vector.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, a sequence that is heterologous to a cell is a sequence that originates from a foreign species, or, if from the same species, is substantially modified in the cell from its native form in composition and/or genomic locus by deliberate human intervention.

It will further be appreciated that appropriate promoter and/or regulatory elements can readily be selected to allow expression of the relevant transcription units in the cell of interest. In certain embodiments, the promoter utilized to direct intracellular expression of a silencing element is a promoter for RNA polymerase III (Pol III). References discussing various Pol III promoters, include, for example, Yu et al. (2002) *Proc. Natl. Acad. Sci.* 99(9), 6047-6052; Sui et al. (2002) *Proc. Natl. Acad. Sci.* 99(8), 5515-5520 (2002); Paddison et al. (2002) *Genes and Dev.* 16, 948-958; Brummelkamp et al. (2002) *Science* 296, 550-553; Miyagashi (2002) *Biotech.* 20, 497-500; Paul et al. (2002) *Nat. Biotech.* 20, 505-508; Tuschl et al. (2002) *Nat. Biotech.* 20, 446-448. According to other embodiments, a promoter for RNA polymerase I, e.g., a tRNA promoter, can be used. See McCown et al. (2003) *Virology* 313(2):514-24; Kawasaki (2003) *Nucleic Acids Res.* 31 (2):700-7.

The regulatory sequences can also be provided by viral regulatory elements. For example, commonly used promoters are derived from polyoma, Adenovirus 2, cytomegalovirus, and Simian Virus 40. For other suitable expression systems for both prokaryotic and eukaryotic cells, see Chapters 16 and 17 of Sambrook et al. (1989) *Molecular Cloning: A Laboratory Manual* (2d ed., Cold Spring Harbor Laboratory Press, Plainview, New York). See, Goeddel (1990) in *Gene Expression Technology: Methods in Enzymology* 185 (Academic Press, San Diego, Calif.).

Various constitutive promoters are known. For example, in various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to help achieve expression of a coding sequence of interest. Promoters which may be used include, but are not limited to, the long terminal repeat as described in Squinto et al. (1991) *Cell* 65:1 20); the SV40 early promoter region (Bernoist and Chambon (1981) *Nature* 290:304 310), the CMV promoter, the M-MuLV 5' terminal repeat the promoter contained in the 3' long terminal repeat of Rous sarcoma virus (Yamamoto et al. (1980) *Cell* 22:787 797), the herpes thymidine kinase promoter (Wagner et al. (1981) *Proc. Natl. Acad. Sci. U.S.A.* 78:144 1445), the regulatory sequences of the metallothionine gene (Brinster et al. (1982) *Nature* 296:39 42); the following animal transcriptional control regions, which exhibit tissue specificity and have been utilized in transgenic animals: elastase I gene control region which is active in pancreatic acinar cells (Swift et al. (1984) *Cell* 38:639 646; Ornitz et al. (1986) *Cold Spring Harbor Symp. Quant. Biol.* 50:399 409; MacDonald, 1987, Hepatology Z:425 515); insulin gene control region which is active in pancreatic beta cells (Hanahan (1985) *Nature* 315:115 122), immunoglobulin gene control region which is active in lymphoid cells (Grosschedl et al. (1984) *Cell* 38:647 658; Adames et al (1985) *Nature* 318:533 538; Alexander et al. (1987) *Mol. Cell. Biol.* 7:1436 1444), mouse mammary tumor virus control region which is active in testicular, breast, lymphoid and mast cells (Leder et al. (1986) *Cell* 45:485 495).

Inducible promoters are also known. Non-limiting examples of inducible promoters and their inducer include MT II/Phorbol Ester (TPA) (Palmiter et al. (1982) *Nature* 300:611) and heavy metals (Haslinger and Karin (1985) *Proc. Nat'l Acad. Sci. USA.* 82:8572; Searle et al. (1985) *Mol. Cell. Biol.* 5:1480; Stuart et al. (1985) *Nature* 317:828; Imagawa et al. (1987) *Cell* 51:251; Karin et al. (1987) *Mol. Cell Biol.* 7:606; Angel et al. (1987) *Cell* 49:729; McNeall et al. (1989) *Gene* 76:8); MMTV (mouse mammary tumor virus)/Glucocorticoids (Huang et al. (1981) *Cell* 27:245; Lee et al. (1981) *Nature* 294:228; Majors and Varmus (1983) *Proc. Nat'l Acad Sci. USA.* 80:5866; Chandler et al. (1983) *Cell* 33:489; Ponta et al. (1985) *Proc. Nat'l Acad. Sci. USA.* 82:1020; Sakai et al. (1988) *Genes and Dev.* 2:1144); β-Interferon/poly(rDX and poly(rc) (Tavernier et al. (1983) *Nature* 301:634); Adenovirus 5 E2/E1A (Imperiale and Nevins (1984) *Mol. Cell. Biol.* 4:875); c-jun/Phorbol Ester (TPA), $H_2O_2$; Collagenase/Phorbol Ester (TPA) (Angel et al. (1987)*Mol. Cell. Biol.* 7:2256); Stromelysin/Phorbol Ester (TPA), IL-1 (Angel et al. (1987) *Cell* 49:729); SV40/Phorbol Ester (TPA) (Angel et al. (1987) *Cell* 49:729); Murine MX Gene/Interferon, Newcastle Disease Virus; GRP78 Gene/A23187 (Resendez Jr. et al. (1988) *Mol. Cell. Biol.* 8:4579); α-2-Macroglobulin/IL-6; Vimentin/Serum (Kunz et al. (1989) *Nucl. Acids Res.* 17:1121); MHC Class I Gene H-2 kB/Interferon (Blanar et al. (1989) *EMBO J.* 8:1139); HSP70/Ela, SV40 Large T Antigen (Taylor and Kingston (1990) *Mol. Cell. Biol.* 10:165; Taylor and Kingston (1990) *Mol. Cell. Biol.* 10:176; Taylor et al. (1989) *J. Biol. Chem.* 264:15160); Proliferin/Phorbol Ester-TPA (Mordacq and Linzer (1989) *Genes and Dev.* 3:760); Tumor Necrosis Factor/PMA (Hensel et al. (1989) *Lymphokine Res.* 8:347); Thyroid Stimulating Hormone α Gene/Thyroid Hormone (Chatterjee et al. (1989) *Proc. Nat'l Acad. Sci. USA.* 86:9114); and, Insulin E Box/Glucose.

Such expression cassettes can be contained in a vector which allow for the introduction of the expression cassette into a cell. In specific embodiments, the vector allows for autonomous replication of the expression cassette in a cell or may be integrated into the genome of a cell. Such vectors are replicated along with the host genome (e.g., nonepisomal mammalian vectors). In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses). See, for example, U.S. Publication 2005214851, herein incorporated by reference.

Any expression cassette can further comprise a selection marker. As used herein, the term "selection marker" comprises any polynucleotide, which when expressed in a cell allows for the selection of the transformed cell with the vector. For example, a selection marker can confer resistance to a drug, a nutritional requirement, or a cytotoxic drug. A selection marker can also induce a selectable phenotype such as fluorescence or a color deposit. A "positive selection marker" allows a cell expressing the marker to survive against a selective agent and thus confers a positive selection characteristic onto the cell expressing that marker. Positive selection marker/agents include, for example, Neo/G418, Neo/Kanamycin, Hyg/Hygromycin, hisD/Histidinol, Gpt/Xanthine, Ble/Bleomycin, HPRT/Hypoxanthine. Other positive selection markers include DNA sequences encoding membrane bound polypeptides. Such polypeptides are well known to those skilled in the art and can comprise, for example, a secretory sequence, an extracellular domain, a transmembrane domain and an intracellular domain. When expressed as a positive selection marker, such polypeptides associate with the cell membrane. Fluorescently labeled antibodies specific for the extracellular domain may then be used in a fluorescence activated cell sorter (FACS) to select for cells expressing the membrane bound polypeptide. FACS selection may occur before or after negative selection.

A "negative selection marker" allows the cell expressing the marker to not survive against a selective agent and thus confers a negative selection characteristic onto the cell expressing the marker. Negative selection marker/agents include, for example, HSV-tk/Acyclovir or Gancyclovir or FIAU, Hprt/6-thioguanine, Gpt/6-thioxanthine, cytosine deaminase/5-fluoro-cytosine, diphtheria toxin or the ricin toxin. See, for example, U.S. Pat. No. 5,464,764, herein incorporated by reference.

In preparing an expression cassette or a homologous recombination cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

An "isolated" or "purified" polynucleotide or protein, or biologically active portion thereof, is substantially or essentially free from components that normally accompany or interact with the polynucleotide or protein as found in its naturally occurring environment. Thus, an isolated or purified protein is substantially free of other cellular material, or culture medium when produced by recombinant techniques, or substantially free of chemical precursors or other chemicals when chemically synthesized. An "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

Any cell can be used in the methods and compositions. In specific embodiments, the cell is from a mammal, a primate, a human, a domestic animal or an agricultural animal. In specific embodiment, the cell is a non-human cell. Non-limiting animals that the cell can be derived from include cattle, sheep, goats, pigs, horses, rabbits, dogs, monkeys, cats, large felines (lions, tigers, etc.), wolves, mice, rats, rabbits, deer, mules, bears, cows, pigs, horses, oxen, zebras, elephants, and so on. The cell can further be from a plant, a worm (e.g., *C. elegans*), an insect, a fish, a reptile, an amphibian, a bird (including, but not limited to chickens, turkeys, ducks, geese and the like), a marsupial, etc. The cells can be derived from any tissue (diseased or healthy) from any of these organisms. Expression of IL-35R can be engineered to occur in any cell type that one would want to control growth or proliferation of, especially tumor cells or tissues/cells that are common targets of autoimmune diseases. Such host cells include cultured cells (in vitro), explants and primary cultures (in vitro and ex vivo).

The present invention further provides transgenic animals expressing a first heterologous polynucleotide encoding gp130 or an active variant or fragment thereof and a second heterologous polynucleotide encoding an IL12Rβ2 polypeptide or an active variant or fragment thereof.

Such animals are useful as animal models having modulated IL-35R activity, including for example, animal models having modulated effector T cell function. In general, methods of generating transgenic animals and transformed cell lines are well known in the art (for example, see Grosveld et al., Transgenic Animals, Academic Press Ltd., San Diego, Calif. (1992)). Using the nucleotide sequences disclosed herein encoding gp130 and IL12Rβ2, a skilled artisan can readily generate transgenic animals and transformed cell lines which contain and express both heterologous sequences. Such animals serve as models for the development of alternative therapies for therapies that modulate effector T cell function.

Such methods of the invention involve introducing a polypeptide or polynucleotide into a cell. "Introducing" is intended to mean presenting to the cell the polynucleotide or polypeptide in such a manner that the sequence gains access to the interior of a cell of the plant. The methods of the invention do not depend on a particular method for introducing a sequence into a cell, only that the polynucleotide or polypeptides gains access to the interior of a cell. Methods for introducing polynucleotide or polypeptides into various cell types are known in the art including, but not limited to, stable transformation methods, transient transformation methods, and virus-mediated methods.

"Stable transformation" is intended to mean that the nucleotide construct introduced into a cell integrates into the DNA of the cell and is capable of being inherited by the progeny thereof "Transient transformation" is intended to mean that a polynucleotide is introduced into the cell and does not integrate into the genome of the cell or a polypeptide is introduced into a cell. Transformation protocols as well as protocols for introducing polypeptides or polynucleotide sequences into cell may vary depending on the type of cell targeted for transformation.

Exemplary art-recognized techniques for introducing foreign polynucleotides into a host cell, include, but are not limited to, calcium phosphate or calcium chloride co-precipitation, DEAE-dextran-mediated transfection, lipofection, particle gun, or electroporation and viral vectors. Suitable methods for transforming or transfecting host cells can be found in U.S. Pat. Nos. 5,049,386, 4,946,787; and 4,897,355, Sambrook et al. (1989) *Molecular Cloning: A Laboratory Manual* (2d ed., Cold Spring Harbor Laboratory Press, Plainview, N.Y.) and other standard molecular biology laboratory manuals. Various transfection agents can be used in these techniques. Such agent are known, see for example, WO 2005012487. One of skill will recognize that depending on the method by which a polynucleotide is introduced into a cell, the silencing element can be stably incorporated into the genome of the cell, replicated on an autonomous vector or plasmid, or present transiently in the cell.

Viral vector delivery systems include DNA and RNA viruses, which have either episomal or integrated genomes after delivery to the cell. For a review of viral vector procedures, see Anderson (1992) *Science* 256:808-813; Haddada et al. (1995) *Current Topics in Microbiology and Immunology* Doerfler and Bohm (eds); and Yu et al. (1994) *Gene Therapy* 1:13-26. Conventional viral based systems for the delivery of polynucleotides could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene.

II. Uses, Methods, and Kits

The polynucleotide(s) encoding the IL-35R complex and active variants and fragments thereof, the IL-35R complex and active variants and fragments thereof, the soluble form of the IL-35R complex, the IL-35R specific binding and/or modulating agents, and the IL-35R agonist and antagonists disclosed herein can be used in one or more of the following methods: (a) screening assays; (b) detection assays; (c) predictive medicine (e.g., diagnostic assays, prognostic assays, monitoring clinical trials, and pharmacogenomics); and (d) methods of treatment (e.g., therapeutic and prophylactic).

i. Methods to Screen for IL-35R Binding and/or Modulating

The invention provides a method (also referred to herein as a "screening assay") for identifying binding and/or modulating agents of IL-35R. As discussed above, identification of various IL-35R binding agents are of interest including agonist IL-35R binding agents, antagonist IL-35R binding agents, and IL-35R specific binding agents. Similarly, identification of various IL-35R modulating agents are of interest including, for example, IL-35R agonist and antagonists.

The test compounds employed in the various screening assays can include any candidate compound including, for example, peptides, peptidomimetics, small molecules, antibodies, or other drugs. Such test compounds can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865-1869), or phage (Scott and Smith (1990) *Science* 249:386-390; Devlin (1990) *Science* 249:404-406; Cwirla et al. (1990) *Proc. Natl. Acad. Sci. USA* 87:6378-6382; and Felici (1991) *J Mol. Biol.* 222:301-310).

Determining the ability of the test compound to bind to the IL-35R complex can be accomplished, for example, by coupling the test compound with a radioisotope or enzymatic label such that binding of the test compound to the IL-35R complex or a biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In one embodiment, an assay is a cell-free assay comprising contacting an IL-35R complex or biologically active fragment or variant thereof with a test compound and determining the ability of the test compound to bind to the IL-35R complex or the biologically active variant or fragment thereof. Binding of the test compound to the IL-35R complex can be determined either directly or indirectly. An indirect assay could include assaying for a modulation in IL-35R activity. In a further embodiment, the test or candidate compound specifically binds to or selectively binds to the IL-35R complex.

In another embodiment, the assay includes contacting the IL-35R complex or biologically active variant or fragment thereof with a known compound that binds to the IL-35R complex (such as its ligand, IL-35) to form an assay mixture, contacting the assay mixture with a test compound, and determining the ability of the test compound to preferentially bind to IL-35R complex or biologically active fragment or variant thereof as compared to the known compound.

In another embodiment, an assay comprises contacting the IL-35R complex or biologically active portion thereof with a test compound and determining the ability of the test compound to modulate (e.g., stimulate or inhibit, act as an agonist or antagonist) the activity of the IL-35R complex or biologically active portion thereof. Determining the ability of the test compound to modulate the activity of an IL-35R complex can be accomplished, for example, by determining the ability of the IL-35R complex to bind to its ligand, IL-35, as described above, for determining direct binding. In an alternative embodiment, determining the ability of the test compound to modulate the activity of an IL-35R complex can be accomplished by determining the ability of the IL-35R complex to further modulate intercellular downstream pathways modulated by IL-35R. Such activities are discussed elsewhere herein.

In some assays, it may be desirable to immobilize either an IL-35R complex or a biologically active fragment or variant thereof or the test compound to facilitate separation of complexed from uncomplexed forms of the IL-35R complex, as well as to accommodate automation of the assay. In one embodiment, a fusion protein can be provided that adds a domain that allows the IL-35R complex or active fragment or variant thereof or the test agent to be bound to a matrix. For example, glutathione-S-transferase/IL-35R complex fusion proteins or glutathione-S-transferase/IL-35R complex fusion proteins can be adsorbed onto glutathione sepharose beads (Sigma Chemical, St. Louis, Mo.) or glutathione-derivatized microtitre plates, which are then combined with the test compound, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above.

Other techniques for immobilizing proteins on matrices can also be used in the screening assays of the invention. For example, either the IL-35R complex or active fragment thereof or the test compound can be immobilized utilizing conjugation of biotin and streptavidin. Biotinylated IL-35R complexes or active fragments thereof or test agents can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals).

In yet another aspect of the invention, the IL-35R complex can be used as "bait proteins" in a two-hybrid assay or three-hybrid assay (see, e.g., U.S. Pat. No. 5,283,317; Zervos et al. (1993) *Cell* 72:223-232; Madura et al. (1993) *J Biol. Chem.* 268:12046-12054; Bartel et al. (1993) *Bio/Techniques* 14:920-924; Iwabuchi et al. (1993) *Oncogene* 8:1693-1696; and PCT Publication No. WO 94/10300), to identify other proteins, which bind to or interact with the IL-35R complex or active fragments and variants thereof and, in some embodiments, modulate IL-35R complex activity.

This invention further pertains to novel agents identified by the above-described screening assays and uses thereof for treatments as described herein.

ii. Methods for Detecting

Various methods and compositions for detecting and/or determining the level of expression of a polynucleotide encoding gp130 and IL12Rβ2 in a sample are provided. A biological sample can comprise any sample in which one desires to determine the level of expression of a polynucleotide encoding gp130 and IL12Rβ2 or one desires to detect or quantitate the level of the IL-35R complex. The term "biological sample" is intended to include tissues, cells, and biological fluids isolated from a subject, as well as tissues, cells, and fluids present within a subject. Detection of the expression of IL-35R in any cell type that expresses IL-35R can be performed, including expression levels in either diseased verses healthy tissue. That is, the detection method of the invention can be used to detect gp130 mRNA or genomic DNA, IL12Rβ2 mRNA or genomic DNA, or the IL-35R complex in a biological sample in vitro, as well as, in vivo. For example, in vitro techniques for detection of include Northern hybridizations and in situ hybridizations. In vitro techniques for detection of the IL-35R complex include enzyme linked immunosorbent assays (ELISAs), Western blots, immunoprecipitations, and immunofluorescence. In vitro techniques for detection of genomic DNA include Southern hybridizations. Furthermore, in vivo techniques for detection of the IL-35R complex include introducing into a subject a labeled anti-IL-35R specific antibody. For example, the antibody can be labeled with a radioactive marker whose presence and location in a subject can be detected by standard imaging techniques.

a. Detecting Polynucleotides

In one embodiment, a method for detecting the level of expression of a polynucleotide encoding gp130 or active variants and fragments thereof and IL12Rβ2 or active variants and fragments thereof in a sample comprises contacting the sample with a) a first and a second primer capable of specifically amplifying a first amplicon comprising a polynucleotide encoding a gp130 polypeptide or an active variant or fragment thereof and, b) a third and a fourth primer capable of specifically amplifying a second amplicon comprising a polynucleotide encoding an IL12Rβ2 polypeptide or an active variant or fragment thereof wherein the encoded polypeptides form a biologically active IL-35R complex. The first and the second amplicon is amplified and then detected.

In other embodiments, a method for detecting the level of expression of a polynucleotide encoding gp130 or active variants and fragments thereof and IL12Rβ2 or active variants and fragments thereof in a sample comprises contacting the sample with a) a first polynucleotide capable of specifically detecting a polynucleotide encoding a gp130 polypeptide or an active variant or fragment thereof and, b) a second polynucleotide capable of specifically detecting a polynucleotide encoding an IL12Rβ2 polypeptide or an active variant or fragment thereof wherein the encoded polypeptides form a biologically active IL-35R complex; and detecting the polynucleotide encoding the gp130 polypeptide or an active variant or fragment thereof and detecting the polynucleotide encoding the IL12Rβ2 polypeptide or an active variant or fragment thereof.

In specific embodiments, the sample is contacted with a polynucleotide probe that hybridizes under stringent hybridization conditions to the target sequences to be detected. The sample and probes are then subjected the sample and probe to stringent hybridization conditions and the hybridization of the probe to the target sequences is detected.

Primers and probes are based on the sequence of the polynucleotides encoded by gp130 and IL12Rβ2 or active variants and fragments thereof. Any conventional nucleic acid hybridization or amplification method can be used to identify the presence of the polynucleotides encoded by gp130 and IL12Rβ2 in a sample. By "specifically detect" is intended that the polynucleotide can be used either as a primer to specifically amplify an amplicon of a polynucleotide encoding gp130 or IL12Rβ2 or the polynucleotide can be used as a probe that hybridizes under stringent conditions to a polynucleotide encoding gp130 or IL12Rβ2. The level or degree of hybridization which allows for the specific detection or the specific amplification of a polynucleotide encoding gp130 or IL12Rβ2 is sufficient to distinguish the polynucleotide encoding gp130 or IL12Rβ2 from a polynucleotide that does not encode the recited polypeptide. By "shares sufficient sequence identity or complementarity to allow for the amplification of a polynucleotide encoding gp130 or IL12Rβ2" is intended the sequence shares at least 80%, 85%, 90%, 91%, 92%, 93%, 94%, 95%, 96%, 97%, 98%, 99% or 100% identity or complementarity to a fragment or across the full length of the polynucleotide encoding gp130 or IL12Rβ2.

Regarding the amplification of a target polynucleotide (e.g., by PCR) using a particular amplification primer pair, "stringent conditions" are conditions that permit the primer pair to hybridize to the target polynucleotide to which a primer having the corresponding wild-type sequence (or its complement) would bind and preferably to produce an identifiable amplification product (the amplicon) in a DNA thermal amplification reaction. In a PCR approach, oligonucleotide primers can be designed for use in PCR reactions to amplify a polynucleotide encoding gp130 or IL12Rβ2. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, New York). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Methods of amplification are further described in U.S. Pat. Nos. 4,683,195, 4,683,202 and Chen et al. (1994) *PNAS* 91:5695-5699. These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplified polynucleotide (amplicon) can be of any length that allows for the detection of the polynucleotide encoding gp130 or IL12Rβ2. For example, the amplicon can be about 10, 50, 100, 200, 300, 500, 700, 100, 2000, 3000, 4000, 5000 nucleotides in length or longer.

Any primer can be employed in the methods of the invention that allows a polynucleotide encoding gp130 or IL12Rβ2 to be amplified and/or detected. For example, in specific embodiments, the first primer pair comprises primers comprising a fragment of a polynucleotide encoding gp130, wherein the first primer pair shares sufficient sequence identity or complementarity to the polynucleotide to amplify the polynucleotide encoding gp130; and, the second primer pair comprises primers comprising a fragment of a polynucleotide encoding IL12Rβ2, wherein the first primer pair shares sufficient sequence identity or complementarity to the polynucleotide to amplify the polynucleotide encoding IL12Rβ2. In specific embodiments, the primer can comprise at least 8, 10, 15, 20, 25, 30, 40 or greater consecutive nucleotide of SEQ ID NO: 1, 2, 4 or 5. In order for a nucleic acid molecule to serve as a primer or probe it need only be sufficiently complementary in sequence to be able to form a stable double-stranded structure under the particular solvent and salt concentrations employed.

In hybridization techniques, all or part of a polynucleotide that selectively hybridizes to a target polynucleotide encoding gp130 or IL12Rβ2 is employed. By "stringent conditions" or "stringent hybridization conditions" when referring to a polynucleotide probe is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a polynucleotide that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)—0.61 (% form)—500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.) and Haymes et al. (1985) In: *Nucleic Acid Hybridization, a Practical Approach*, IRL Press, Washington, D.C.

A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

b. Detecting the IL-35R Complex

One aspect of the present invention relates to assays for detecting IL-35R complexes in the context of a biological sample. An exemplary method for detecting the presence or absence or the quantity of the IL-35R complex in a biological sample involves obtaining a biological sample and contacting the biological sample with a compound or an agent capable of specifically binding and detecting an IL-35R complex, such that the presence of the IL-35R complex is detected in the biological sample. Results obtained with a biological sample from a test subject may be compared to results obtained with a biological sample from a control subject.

Detection of IL-35R with an IL-35R specific binding agent allows for the detection, purification, and/or isolation of cell populations expressing IL-35R. Such methods find use in determining cell populations that are sensitive or resistant to the effects of IL-35. Information gained by such techniques can then be used when designing IL-35 treatments or therapies.

In one embodiment, an agent for detecting the IL-35R complex is an antibody capable of specifically binding to the IL-35R complex, preferably an antibody with a detectable label. Antibodies can be polyclonal, or more preferably, monoclonal. An intact antibody, or a fragment thereof (e.g., Fab or $F(abN)_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody.

iii. Kits

As used herein, "kit" refers to a set of reagents for the identification and/or the detection of the polynucleotide encoding gp130 or IL12Rβ2 or detection and/or quantitation of the IL-35R complex in biological samples. The terms "kit" and "system," as used herein are intended to refer to at least one or more detection reagents which, in specific embodiments, are in combination with one or more other types of elements or components (e.g., other types of biochemical reagents, containers, packages, such as packaging intended for commercial sale, substrates to which detection reagents are attached, electronic hardware components, instructions of use, and the like).

In one embodiment, a kit for determining the level of expression of a polynucleotide encoding gp130 and IL12Rβ2 in a sample is provided. The kit comprises a) a first polynucleotide capable of specifically detecting or amplifying a polynucleotide encoding a first polypeptide encoding gp130 or a biologically active variant or fragment thereof; and, b) a second polynucleotide capable of specifically detecting or amplifying a polynucleotide encoding IL12Rβ2 or a biologically active variant or fragment thereof, wherein the encoded polypeptides form a biologically active IL-35R complex.

In specific embodiments, the kit comprises a) a first and a second primer that share sufficient sequence homology or complementarity to the polynucleotide encoding gp130 or the active variant or fragment thereof to specifically amplify the polynucleotide encoding gp130; and, b) a third and a forth primer that share sufficient sequence homology or complementarity to a polynucleotide encoding IL12Rβ2 or an active variant or fragment thereof to specifically amplify the polynucleotide encoding IL12Rβ2.

In still other embodiments, the kit comprises a) a first probe that can specifically detect the polynucleotide encoding gp130 or the active variant or fragment thereof, wherein the first probe comprises at least one polynucleotide of a sufficient length of contiguous nucleotides identical or complementary to the polynucleotide encoding gp130 or the active variant thereof; and, b) a second probe that can specifically detect a second polynucleotide encoding IL12Rβ2 or an active variant or fragment thereof, wherein the second probe comprises at least one polynucleotide of a sufficient length of contiguous nucleotides identical or complementary to a polynucleotide encoding IL12Rβ2 or an active variant or fragment thereof. In still further embodiments, the first polynucleotide hybridizes under stringent conditions to the sequence encoding the gp130 polypeptide or active variant thereof; and, the second polynucleotide hybridizes under stringent conditions to the sequence encoding IL12Rβ2 or an active variant or fragment thereof.

In still other embodiments, a kit for determining the presence of Interleukin 35 Receptor (IL-35R) in a sample is provided. Such a kit can comprises any IL-35R specific binding and/or IL-35R specific binding/modulating agent disclosed herein, including, but not limited to one or more of the IL-35R specific antibodies disclosed herein or any mixture thereof.

iv. Methods for Modulating the Activity of the IL-35R Complex

Methods for modulating (i.e., inducing, inhibiting, potentiating, elevating, increasing, decreasing) the activity of the IL-35R complex or modulating effector T-cell function are provided. Such methods can comprise contacting a cell expressing the IL-35R complex with an IL-35R antagonists or agonists.

As used herein, "responder T cells" or "effector T cells" refer to a subpopulation of mature T cells that facilitate an immune response through cell activation and/or the secretion of cytokines. As used herein, "effector T cells" include cytotoxic T cells (Tc), including for example, CD8+ cells, and helper T cells (Th1 cells, Th2 cells, CD4+, Th17, Th9, and gamma delta T-cells). As used herein, "effector T cell function" includes an activity exerted by an effector T cell, as determined in vitro or in vivo, according to standard techniques. In one embodiment, the effector T cell function includes the elimination of an antigen by, for example, the production of cytokines preferentially associated with effector T cells, which modulate the activation of other cells, or by cytotoxic activity. In one embodiment, an effector T cell function is a cytotoxic (or cytolytic) T cell (Tc or CTL) function, such as, for example, cytolysis of cells infected with microbes. In another embodiment, an effector T cell function is a Th1 cell function, e.g., mediation of delayed type hypersensitivity responses and macrophage activation. In yet another embodiment, an effector T cell function is a Th2 cell function, e.g., help to B cells (Mosmann et al. (1989) *Annu. Rev. Immunol.* 7, 145-173; Paul et al. (1994) *Cell* 76, 241-251; Arthur and Mason (1986) *J Exp. Med.* 163, 774-786; Paliard et al. (1988) *J Immunol.* 141, 849-855; Finkelman et al., (1988) *J. Immunol.* 141, 2335-2341). In another embodiment, an effector T cell function includes an inflammatory response, the suppression of immunological tolerance, or "tipping the balance" toward a proliferative/stimulatory environment. For purposes of the invention, effector T cell function is enhanced or inhibited by a statistically significant amount, for example, by at least 5%, at least 10%, at least 15%, at least 20%, at least 30%, at least 50%, at least 60%, at least 70%, at least 80%, or at least 90% as compared to an appropriate control cells.

An IL-35R agonist will act to suppress or inhibit effector T-cell activity. The agonist can be, for example, an IL-35R specific binding/modulating agent or an IL-35R specific modulating agent. By "inhibiting or suppressing an effector T cell function in a subject" is intended reducing and/or blocking of one or more of the functions mediated by effector T cells. Thus, in one embodiment, a method of suppressing an effector T cell function is provided and comprises administering to the subject a therapeutically effective amount of an Interleukin 35 Receptor (IL-35R) agonist.

For example, an IL-35R agonist promotes immune tolerance, which can find use, for example, in treating a subject having an autoimmune or an inflammatory disorder, including but not limited to, graft rejections and allergies. Thus, in one embodiment, a method of treating a subject having an autoimmune or inflammatory disorder is provided. Such a method comprises administering to the subject a therapeutically effective amount of an agonist Interleukin 35 Receptor (IL-35R) agent. Various agonist Interleukin 35 Receptor (IL-35R) agents and method for preparing such agents are discuses elsewhere herein. In specific embodiments, the agonist agent is an antibody or a small molecule. Examples of autoimmune diseases include, for example, type 1 diabetes, rheumatoid arthritis and multiple sclerosis. Inflammatory disorders that may be treated include, for example, asthma and inflammatory bowel disease. In addition, limiting IL-35 by IL-35 antagonist could help enhance anti-tumor immunity elicited by effector T cells.

In other embodiments, the IL-35R agonist can be used in combination with a therapeutic agent to reduce the immune response to the agent (i.e., protein). For example, the IL-35R agonist can be used in combination with a therapeutic protein which must be chronically administered to a subject. Thus, in a specific embodiment, the method comprises includes administering to the subject at least one additional therapeutic agent in combination with an IL-35R agonist. Such therapeutic agents, include but are not limited to, a cytokine, a glucocorticoid, an anthracycline (e.g., doxorubicin or epirubicin), a fluoroquinolone (e.g., ciprofloxacin), an antifolate (e.g., methotrexate), an antimetabolite (e.g., fluorouracil), a topoisomerase inhibitor (e.g., camptothecin, irinotecan or etoposide), an alkylating agent (e.g., cyclophosphamide, ifosfamide, mitolactol, or melphalan), an antiandrogen (e.g., flutamide), an antiestrogen (e.g., tamoxifen), a platinum compound (e.g., cisplatin), a vinca alkaloid (e.g., vinorelbine, vinblastine or vindesine), a mitotic inhibitor (e.g., paclitaxel or docetaxel), an inhibitor of the PI3K/Akt/mTOR pathway, such as rapamycin, and/or an inhibitor of calcineurin.

An IL-35R antagonist will act to enhance or promote effector T-cell activity. The antagonist can be, for example, an IL-35R specific binding/modulating agent or an IL-35R specific modulating agent. By "enhancing an effector T cell function in a subject" is intended reducing and/or blocking one or more of the functions mediated by effector T cells. For example, an IL-35R antagonist will act to increase or potentiate at least one effector T cell function and thereby increase the immune response. Thus, in one embodiment, a method of increasing an effector T cell function is provided and comprises administering to the subject a therapeutically effective amount of an antagonistic Interleukin 35 Receptor (IL-35R) agent.

Such IL-35R antagonists find use in treating any conditions in which the IL-35 mediated activity of the T regulatory cells is shown to be blocking or limiting disease resolution. For example, the IL-35R antagonists find use when activation of effector responses is desired such as in cases of acute infection, vaccine response, anti-tumor immunity or treating cancer. Thus, in one embodiment, a method of treating a subject having a cancer or acute infection is provided. Such a method comprises administering to the subject a therapeutically effective amount of an antagonistic Interleukin 35 Receptor (IL-35R) agent. Various antagonistic Interleukin 35 Receptor (IL-35R) agents and method for preparing such agents are discuses elsewhere herein. In specific embodiments, the antagonist agent is an antibody or a small molecule.

It is further recognized that the various IL-35R antagonists can be used in combination with an antigen to enhance the immune response to the antigen. For example, T effector cell responses employing an IL-35R antagonist can be used to enhance a vaccine preparation. Thus, the various IL-35R antagonist are useful for increasing the efficacy of anticancer vaccines or for vaccines that are poorly immunogenic.

Thus, further provided are methods for enhancing the efficacy or immunogenicity of a vaccine in a subject, or overcoming a suppressed immune response to a vaccine in a subject, including (i) administering to the subject a therapeutically effective amount of an antagonist IL-35R agent and (ii) administering to the subject a vaccine. In specific embodiments, the antagonist is an IL-35R specific binding/modulating agent. In one embodiment, the vaccine is a cancer vaccine. For example, immune responses are suppressed in cancer and chronic infections and thus combining IL-35R agonists with therapeutic cancer vaccines or vaccines against chronic infections such as HCV, HIV and TB could improve efficacy.

By "vaccine" is intended a composition useful for stimulating a specific immune response (or immunogenic response) in a subject. In some embodiments, the immunogenic response is protective or provides protective immunity. For example, in the case of a disease-causing organism the vaccine enables the subject to better resist infection with or disease progression from the organism against which the vaccine is directed. Alternatively, in the case of a cancer, the vaccine strengthens the subject's natural defenses against cancers that have already developed. These types of vaccines may also prevent the further growth of existing cancers, prevent the recurrence of treated cancers, and/or eliminate cancer cells not killed by prior treatments.

Representative vaccines include, but are not limited to, vaccines against diphtheria, tetanus, pertussis, polio, measles, mumps, rubella, hepatitis B, *Haemophilus influenzae* type b, varicella, meningitis, human immunodeficiency virus, tuberculosis, Epstein Barr virus, malaria, hepatitis E, dengue, rotavirus, herpes, human papillomavirus, and cancers. Vaccines of interest include the two vaccines that have been licensed by the U.S. Food and Drug Administration to prevent virus infections that can lead to cancer: the hepatitis B vaccine, which prevents infection with the hepatitis B virus, an infectious agent associated with liver cancer (*MMWR Morb. Mortal. Wkly. Rep.* 46:107-09, 1997); and Gardasil™, which prevents infection with the two types of human papillomavirus that together cause 70 percent of cervical cancer cases worldwide (Speck and Tyring, *Skin Therapy Lett.* 11:1-3, 2006). Other treatment vaccines of interest include therapeutic vaccines for the treatment of cervical cancer, follicular B cell non-Hodgkin's lymphoma, kidney cancer, cutaneous melanoma, ocular melanoma, prostate cancer, and multiple myeloma.

By "enhancing the efficacy" or "enhancing the immunogenicity" with regard to a vaccine is intended improving an outcome, for example, as measured by a change in a specific value, such as an increase or a decrease in a particular parameter of an activity of a vaccine associated with protective immunity. In one embodiment, enhancement refers to at least a 25%, 50%, 100% or greater than 100% increase in a particular parameter. In another embodiment, enhancement refers to at least a 25%, 50%, 100% or greater than 100% decrease in a particular parameter. In one example, enhancement of the efficacy/immunogenicity of a vaccine refers to an increase in the ability of the vaccine to inhibit or treat disease progression, such as at least a 25%, 50%, 100%, or greater than 100% increase in the effectiveness of the vaccine for that purpose. In a further example, enhancement of the efficacy/immunogenicity of a vaccine refers to an increase in the ability of the vaccine to recruit the subject's natural defenses against cancers that have already developed, such as at least a 25%, 50%, 100%, or greater than 100% increase in the effectiveness of the vaccine for that purpose.

Similarly, by "overcoming a suppressed immune response" with regard to a vaccine is intended improving an outcome, for example, as measured by a change in a specific value, such as a return to a formerly positive value in a particular parameter of an activity of a vaccine associated with protective immunity. In one embodiment, overcoming refers to at least a 25%, 50%, 100% or greater than 100% increase in a particular parameter. In one example, overcoming a suppressed immune response to a vaccine refers to a renewed ability of the vaccine to inhibit or treat disease progression, such as at least a 25%, 50%, 100%, or greater than 100% renewal in the effectiveness of the vaccine for that purpose. In a further example, overcoming a suppressed immune response to a vaccine refers to a renewed ability of the vaccine to recruit the subject's natural defenses against cancers that have already developed, such as at least a 25%, 50%, 100%, or greater than 100% renewal in the effectiveness of the vaccine for that purpose.

A therapeutically effective amount of an IL-35R antagonist or agonist can be administered to a subject. By "therapeutically effective amount" is intended an amount that is useful in the treatment, prevention or diagnosis of a disease or condition. As used herein, a therapeutically effective amount of an IL-R35 agonist or antagonist is an amount which, when administered to a subject, is sufficient to achieve a desired effect, such as modulating (inhibiting or promoting) effector T cell function in a subject being treated with that composition without causing a substantial cytotoxic effect in the subject. The effective amount of an IL-35R-agonist or antagonist useful for modulating effector T-cell function will depend on the subject being treated, the severity of the affliction, and the manner of administration of the IL-35R-agonist or antagonist.

By "subject" is intended mammals, e.g., primates, humans, agricultural and domesticated animals such as, but not limited to, dogs, cats, cattle, horses, pigs, sheep, and the like. Preferably the subject undergoing treatment with the pharmaceutical formulations of the invention is a human.

When administration is for the purpose of treatment, administration may be for either a prophylactic or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an IL-35R agonist or antagonist can include a single treatment or, preferably, can include a series of treatments. It will also be appreciated that the effective dosage of an IL-35R agonist or antagonist used for treatment may increase or decrease over the course of a particular treatment. Changes in dosage may result and become apparent from the results of diagnostic assays as described herein.

It is understood that appropriate doses of such active compounds depends upon a number of factors within the knowledge of the ordinarily skilled physician, veterinarian, or researcher. The dose(s) of the active compounds will vary, for example, depending upon the identity, size, and condition of the subject or sample being treated, further depending upon the route by which the composition is to be administered, if applicable, and the effect which the practitioner desires the active compound to have upon the IL-35R complex. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of an active agent depend upon the potency of the active agent with respect to the expression or activity to be modulated. Such appropriate doses may be determined using the assays described herein. When one or more of these small molecules is to be administered to an animal (e.g., a human) in order to modulate activity of the IL-35R complex, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Therapeutically effective amounts of an IL-35R-specific binding and/or modulating agent can be determined by animal studies. When animal assays are used, a dosage is administered to provide a target tissue concentration similar to that which has been shown to be effective in the animal assays. It is recognized that the method of treatment may comprise a single administration of a therapeutically effective amount or multiple administrations of a therapeutically effective amount of the IL-35R agonist or antagonist.

Any delivery system or treatment regimen that effectively achieves the desired effect of modulating effector T cell function can be used. Thus, for example, formulations comprising an effective amount of a pharmaceutical composition of the invention comprising IL-35R agonists or antagonists can be used for the purpose of treatment, prevention, and diagnosis of a number of clinical indications related to the activity of the IL-35R complex.

v. Pharmaceutical Compositions

The IL-35R complexes or active fragments and variants thereof, soluble forms of the IL-35R complex or active variants and fragments thereof, the IL-35R specific binding agents, and/or the IL-35R antagonist or agonists (also referred to herein as "active compounds") disclosed herein can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. In addition, it may be desirable to administer a therapeutically effective amount of the pharmaceutical composition locally to an area in need of treatment (e.g., to an area of the body where inhibiting a regulatory T ($T_R$) cell function is desired). This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In one embodiment, administration can be by direct injection at the site (or former site) of a cancer that is to be treated. In another embodiment, the therapeutically effective amount of the pharmaceutical composition is delivered in a vesicle, such as liposomes (see, e.g., Langer, *Science* 249:1527-33, 1990 and Treat et al., in *Liposomes in the Therapy of Infectious Disease and Cancer*, Lopez Berestein and Fidler (eds.), Liss, N.Y., pp. 353-65, 1989).

In yet another embodiment, the therapeutically effective amount of the pharmaceutical composition can be delivered in a controlled release system. In one example, a pump can be used (see, e.g., Langer, *Science* 249:1527-33, 1990; Sefton, *Crit. Rev. Biomed. Eng.* 14:201-40, 1987; Buchwald et al., *Surgery* 88:507-16, 1980; Saudek et al., *N. Engl. J. Med.* 321:574-79, 1989). In another example, polymeric materials can be used (see, e.g., Levy et al., *Science* 228:190-92, 1985; During et al., *Ann. Neurol.* 25:351-56, 1989; Howard et al., *J. Neurosurg.* 71:105-12, 1989). Other controlled release systems, such as those discussed by Langer (*Science* 249:1527-33, 1990), can also be used.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor ELΘ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

IV. Sequence Identity

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

As used herein, the singular terms “a,” “an,” and “the” include plural referents unless context clearly indicates otherwise. Similarly, the word “or” is intended to include “and” unless the context clearly indicates otherwise. It is further to be understood that all base sizes or amino acid sizes, and all molecular weight or molecular mass values, given for nucleic acids or polypeptides are approximate, and are provided for description.

The subject matter of the present disclosure is further illustrated by the following non-limiting examples.

EXPERIMENTAL

Example 1

IL-35 Signaling and Suppression Mediated by IL-35 Require the Expression of the IL-35R Materials and Methods:

Mice. C57BL/6 (wild type), CD4.cre, and IL12R$\beta$2$^{-/-}$ mice were purchased from the Jackson Laboratory. Gp130 floxed knockin mice were provided by Rodger McEver at Oklahoma Medical Research Foundation. gp130.fl×CD4.cre×IL12Rb2$^{-/-}$ were obtained by breeding the three mouse strains listed. All animal experiments were performed in American Association for the Accreditation of Laboratory Animal Care-accredited, specific-pathogen-free facilities in the St. Jude Animal Resource Center following national, state and institutional guidelines. Animal protocols were approved by the St Jude Animal Care and Use Committee.

$T_{conv}$ Cell Purification. $T_{eff}$ (CD4$^{+}$CD25$^{-}$CD45RB$^{hi}$) from the spleens and lymph nodes of C57BL/6 or knockout age-matched gp130.fl×CD4.cre×IL12Rb2$^{-/-}$ mice were positively sorted by FACS. After red blood cell lysis, cells were stained with antibodies against CD4, CD25 and CD45RB and purified on a MoFlo cell sorter.

Transfection of HEK293T Cells for IL-35 Protein Generation. IL-35 constructs were generated by recombinant PCR and cloned into pPIGneo, a pCIneo-based vector (Promega) that we have modified to include an IRESGFP cassette. HEK293T cells were transfected using 10 μg plasmid per 2×10$^{6}$ cells using Trans IT transfection reagent. Cells were sorted for equivalent GFP expression and were cultured for 36 hours to facilitate protein secretion. Dialyzed, filtered supernatant from cells was used as the source of IL-35 in IL-35 mediated suppression assays.

i$T_R$35 Conversion. iTr35 are an induced regulatory T cell population that is generated by treatment with IL-35 and suppress via IL-35. See, U.S. Provisional Application No. 61/156,995, herein incorporated by reference in its entirety. Purified murine $T_{eff}$ cells were activated by anti-CD3-+anti-CD28-coated latex beads in the presence of IL-35 supernatant, at 25% of total culture medium, to induce “conversion” of $T_{eff}$ cells into i$T_R$35. Following conversion, i$T_R$35 were purified for use in suppression assays.

In Vitro Suppression by IL-35 and i$T_R$35. $T_{eff}$ were activated for 72 hours with anti-CD3-+anti-CD28-coated latex beads in the presence of IL-35 supernatant as 25%, 12.5%, or 6.25% of culture media. In parallel, i$T_R$35 were purified and assayed for their capacity to suppress freshly sorted $T_{eff}$ cell proliferation. Cultures were pulsed with 1 mCi [$^3$H]-thymidine for the final 8 hours of the 72 hour assay, and were harvested with a Packard Micromate cell harvester. Counts per minute were determined using a Packard Matrix 96 direct counter. Percent suppression was calculated using the following formula: ((cpm of $T_{eff}$ cells alone—cpm of $T_{eff}$ cells treated with IL-35 or i$T_R$35)/cpm of $T_{eff}$ cells alone)*100.

Discussion/Conclusion:

FIG. 1 shows that wild-type $T_{eff}$ proliferation is potently suppressed by IL-35 in a titratable manner. However, IL-35 is unable to suppress the proliferation of $T_{eff}$ cells that lack the IL-35R (gp130.fl×CD4.cre×IL12Rb2$^{-/-}$). i$T_R$35 suppression of $T_{eff}$ cell proliferation is dependent upon IL-35. As such, IL-35R deficient $T_{eff}$ cells are resistant to suppression mediated by i$T_R$35. These results demonstrate that IL-35 signaling and suppression mediated by IL-35 require the expression of the IL-35R.

Example 2

IL-35 Signals Primarily Through Two Different STAT Proteins, STAT1 and STAT4

Materials and Methods:

Mice. Spleens and lymph nodes from Il12rb1$^{-/-}$ mice were provided by D. Fairweather and J. A. Frisancho (Johns Hopkins University), CD4$^{cre}$×gp130$^{fl/fl}$ mice were provided by M. Karin and S. Grivennikov (University of California at San Diego), IL27ra$^{-/-}$ mice were provided by C. Hunter and J. Stumhofer (University of Pennsylvania), Stat1$^{-/-}$ mice were provided by A. Satoskar and P. Reville (Ohio State University), and Stat3$^{-/-}$ mice were provided by C. Drake and H. R. Yen (Johns Hopkins University). IL12rb2$^{-/-}$, Stat4$^{-/-}$, Rag1$^{-/-}$, C57BL/6, B6.PL and Balb/c mice were purchased from the Jackson Laboratory. All animal experiments were performed in American Association for the Accreditation of Laboratory Animal Care-accredited, specific-pathogen-free facilities in the St. Jude Animal Resource Center following national, state and institutional guidelines. Animal protocols were approved by the St. Jude Animal Care and Use Committee.

Neutralizing IL-35 mAb. Neutralizing IL-35 mAb was developed by immunization with recombinant murine Ebi3 protein. Briefly, recombinant murine Ebi3 was cloned and expressed in a proprietary *E. coli* expression system developed by Mike Jones (Shenandoah Biotechnology) and used for immunization of Ebi3$^{-/-}$ mice. Clones V1.4F5.29, V1.4H6.25, and V1.4C4.22 were subsequently chosen for their capacity to IP, blot, and specifically neutralize IL-35 bioactivity.

Transfection of HEK293T cells for IL-35 and control protein generation. IL-35 constructs were generated by recombinant PCR and cloned into pPIGneo, a pCIneo-based vector (Promega) that has been modified to include an IRESGFP cassette. A construct containing Ebi3 and Il12a linked by a flexible glycine-serine linker was used for IL-35 generation and an empty pPIGneo vector was used as a control. HEK293T cells were transfected using 10 μg plasmid per 2×10$^{6}$ cells using TransIT transfection reagent (Mirus). Transfection media was exchanged for fresh culture media after 24 hours and were cultured for an additional 36 hours to facilitate protein secretion. Dialyzed, filtered supernatant from cells was used at 25% of total culture medium to induce conversion of $T_{conv}$ cells into i$T_R$35 or i$T_R$ control cells.

Anti-CD3/CD28-coated latex beads. 4 μM sulfate latex beads (Molecular Probes) were incubated overnight at room temperature with rotation in a 1:4 dilution of anti-CD3+anti- CD28 antibody mix (13.3 μg/ml anti-CD3 (murine clone #145-2c11, human clone # OKT3) (eBioscience) and 26.6 μg/ml anti-CD28 (murine clone #37.51, human clone # CD28.6) (eBioscience). Beads were washed 3 times with 5 mM phosphate buffer pH 6.5 and resuspended at $5\times10^7$/ml in sterile phosphate buffer with 2 mM BSA.

Recombinant IL-35 beads. Beads were generated that presented IL-35 to cells in a manner that excluded use of 293T supernatants. Anti-p35 mAb clone 25806 (R&D Systems) or isotype control (rat IgG2) mAb was added to 1 ml of IL-35 supernatant or control supernatant and rotated at 4° C. for 4 hours. Protein G beads were added and rotated for an additional 12-18 hours. To ensure the protein was attached to the beads, the beads were boiled to release bound protein, resolved by SDS-PAGE and probed with anti-Ebi3 mAb. Both the beads and post IP supernatant were tested for functional activity in a standard suppression assay. Beads were cultured with $T_{conv}$ in medium containing anti-CD3+ anti-CD28 conjugated beads as indicated for 3 days. Proliferation was determined by [$^3$H]-thymidine incorporation.

$T_{conv}$ purification, $iT_R35$ conversion and suppressed $T_{conv}$ cell generation. $T_{conv}$ ($CD4^+CD25^-CD45RB^{hi}$) and $T_{reg}$ ($CD4^+CD25^+CD45RB^{lo}$) cells from the spleens and lymph nodes of C57BL/6 or knockout age-matched mice were positively sorted by FACS. After red blood cell lysis, cells were stained with antibodies against CD4, CD25 and CD45RB (Biolegend) and sorted on a MoFlo (Dako) or Reflection (i-Cyt). Murine $iT_R35$ cells were generated. Briefly, purified murine $T_{conv}$ cells from wild-type or indicated knockout mice were activated by anti-CD3-+anti-CD28-coated latex beads in the presence of 25% culture medium from control or IL-35 transfected 293T cells (dialyzed against media and filtered) to generate murine $iT_R35$. To generate suppressed $T_{conv}$, purified $T_{conv}$ cells were activated in the presence of anti-CD3-+anti-CD28-coated latex beads and $T_{regs}$ at a 4:1 ($T_{conv}$:$T_{reg}$ ratio) for 72 hours. Suppressed $T_{conv}$ from the co-culture were re-sorted on the basis of congenic markers and used for qPCR analysis of receptor expression.

Immunoprecipitation and Western Blotting. Following 18 hour activation with anti-CD3+anti-CD28 coated beads, cells were treated with 100 ng/ml IL12, IL27 or IL35 for indicated times. Whole cell lysates were lysed in cold RIPA buffer and subjected to immunoblotting with antibodies for pSTAT1, pSTAT3, pSTAT4 and pSTAT5 (Cell Signaling Technology and Santa Cruz Biotechnology). Blots were developed using ECL (Amersham Biosciences) and autoradiography.

In Vitro proliferation and suppression assays. To determine proliferative capacity of cells generated as described above, $2.5\times10^4$ cells were activated with anti-CD3-+anti-CD28-coated latex beads for 72 hours. Cultures were pulsed with 1 mCi [$^3$H]-thymidine for the final 8 hours of the 72 hour assay, and were harvested with a Packard Micromate cell harvester. Counts per minute were determined using a Packard Matrix 96 direct counter (Packard Biosciences). For suppression assays, IL-35 supernatants, IL-35 beads or $iT_R35$ were titrated into $T_{conv}$ cell proliferation assays as indicated. Cultures were pulsed and harvested as described for proliferation assays.

$iT_R35$-mediated control of homeostatic expansion. Homeostasis assays were performed. Naive Thy1.2$^+$ $T_{conv}$ cells were isolated by FACS from wild-type or knockout mice (as indicated) and used as "responder" cells in adoptive transfer. Thy1.1$^+$ $iT_R35$ were generated as described above and used as "suppressor" cells in adoptive transfer. $T_{conv}$ cells ($2\times10^6$) with or without suppressor cells ($5\times10^5$) were resuspended in 0.5 ml of PBS plus 2% FBS, and were injected intravenously through the tail vein into $Rag1^{-/-}$ mice. Mice were euthanized seven days post transfer, and splenocytes were counted, stained and analyzed by flow cytometry using antibodies against Thy1.1 and Thy1.2 (BD Bioscience). For each group, 5-10 mice were analyzed.

B16 tumor model. For T cell adoptive transfer experiments using the B16 melanoma model, $Rag1^{-/-}$ mice received indicated cells via the tail vein on day −1 of experiment. Wild type or receptor deficient nave $CD4^+CD25^-$ ($9\times10^6$/mouse) and $CD8^+$ T cells ($6\times10^6$/mouse) alone or in combination with $iT_R35$ cells ($10^6$/mouse) were adoptively transferred into mice. B16-F10 melanoma was a gift from Mary Jo Turk (Dartmouth College, Hanover, N.H.) and was passaged intradermally (i.d.) in C57/Bl6 mice 5 times to ensure reproducible growth. B16 cells were cultured in RPMI 1640 containing 7.5% FBS and washed three times with RPMI prior to injections if viability exceeded 96%. $Rag1^{-/-}$ mice were injected with 120,000 cells on the right flank i.d. B16 tumor diameters were measured daily with calipers and reported as mm$^3$ ($a^2\times b/2$, where "a" is the smaller caliper measurement and "b" the larger). For all experiments, B16 tumors were excised at day 14 when tumor size was 5-10 mm in diameter. For each group, 4-5 mice were analyzed.

The IL35 Receptor Comprises IL12Rβ2 and Gp130.

To determine which IL12 family receptor chains are required for IL-35 mediated suppression, three approaches were utilized, all of which yielded similar results. The use of genetically deficient mice to determine functions of proteins has been extremely useful in defining protein activity. Therefore, it was first assessed whether IL-35 could suppress the proliferation of $CD4^+$ $T_{conv}$ cells that lacked expression of each of the IL12 family receptor chains. $T_{conv}$ cells purified by FACS from wild-type (C57BL/6), CD4'×gp130$^{fl/fl}$ (abbreviated gp130$^{\Delta T}$), $Il27ra^{-/-}$, $Il12rb1^{-/-}$, $^{Il}12rb2^{-/-}$, or $Il12rb2^{-/-}$×CD4$^{cre}$× gp130$^{fl/fl}$ (abbreviated IL35R$^{\Delta T}$) mice were activated with anti-CD3-+anti-CD28-coated latex beads for 3 days in the presence of indicated concentrations of IL-35 or $iT_R35$ in combination with neutralizing IL-35 mAb or isotype control mAb. Proliferation was determined by [$^3$H]-thymidine incorporation. $T_{conv}$ were treated with or without rIL-27 for 18 hours prior to analysis of receptor expression and proliferation. RNA was extracted, cDNA generated and qPCR performed. Cytokine treated cells were mixed at indicated concentrations of IL-35 for 3 days. Proliferation was determined by [$^3$H]-thymidine incorporation.

IL-35 can suppress the proliferation of both $Il27ra^{-/-}$ and $Il12rb1^{-/-}$ $T_{conv}$ cells to a degree similar to that seen in wild-type $T_{conv}$ cells (data not shown). However, $T_{conv}$ cells that lack expression of either IL12Rβ2 ($Il12rb2^{-/-}$) or gp130 (CD4$^{cre}$×gp130$^{fl/fl}$; referred to herein as gp130$^{\Delta T}$) are partially resistant to IL-35 mediated suppression. Generation of $Il12rb2^{-/-}$ and CD4$^{cre}$×gp130$^{fl/fl}$ mice (referred to herein as IL35R$^{\Delta T}$) results in $T_{conv}$ cells that are completely resistant to IL-35 mediated suppression. Many cytokines that signal through the gp130 chain, including LIF, OncM and CNTF, require leukocyte inhibitory factor-β (LIFRβ) in addition to gp130 and the specificity-determining receptor chain. To determine whether IL-35 might also utilize LIFRβ, LIFRβ expression in $T_{conv}$ cells was examined. Quantitative real-time PCR analysis suggests that $T_{conv}$ cells, the targets of IL-35 signaling, do not express LIFRβ, therefore it doesn't appear to be important for IL-35 signaling.

Second, IL-35 conjugated via an anti-p35 specific mAb, or isotype control mAb, to Protein G beads was utilized as suppressors of $T_{conv}$ cell proliferation. Isotype control or non-neutralizing anti-IL35 mAb were incubated with IL-35 supernatant and then coupled with protein G beads. The protein G coupled beads were then incubated with $T_{conv}$ cells activated in presence of α CD3 and α CD28. $T_{conv}$ sorted from indicated wild-type or receptor deficient $T_{conv}$ cells were activated in the presence of wild-type Tregs and proliferation determined by [$^3$H]-thymidine incorporation. For a media alone control, nTreg, or $T_{conv}$ cells mixed at a 4:1 ratio were activated in the presence of anti-CD3-CD28-coated beads in the top chamber of a Transwell™ culture plate. Responder $T_{conv}$ were activated with anti-CD3-CD28-coated beads in the bottom chamber of the plates. Proliferation of the responder $T_{conv}$ cells in the bottom chambers was determined. No suppression of proliferation was detected in isotype control beads, regardless of genotype. However, as seen with both IL-35 protein and $iT_R35$, suppression was limited in IL12Rβ2 and gp130 deficient $T_{conv}$ cells and completely absent in $T_{conv}$ cells that lack both IL12Rβ2 and gp130. It was previously shown that natural $T_{regs}$ that lack IL-35 expression (Ebi3$^{-/-}$ or Il12a$^{-/-}$) are partially defective both in vitro and in vivo (Collison et al. (2007) Nature 450:566-569). Therefore, it was expected that $T_{conv}$ cells that lack the IL-35R and, thus, are unable to respond to IL-35, would be partially resistant to $T_{reg}$-mediated suppression. Indeed, gp130$^{\Delta T}$, Il12rb2$^{-/-}$ and IL35R$^{\Delta T}$ $T_{conv}$ cells are all partially resistant to $T_{reg}$ mediated suppression of proliferation (data not shown). It was previously shown that $T_{conv}$ cells activated in the presence of $T_{reg}$ are potently suppressive across a permeable membrane in an IL-35-dependent manner (Collison et al. (2009). J. Immunol. 182:6121-6128). Therefore, in addition to a standard suppression assay, it was also determined whether IL35R$^{\Delta T}$ $T_{conv}$ were suppressed across a permeable membrane. While wild-type $T_{conv}$ cells were potently suppressed by co-cultured $T_{conv}$ and $T_{reg}$, IL35R$^{\Delta T}$ $T_{conv}$ cells were completely resistant to $iT_R35$ mediated suppression (data not shown).

Third, a novel induced $T_{reg}$ population, $iT_R35$, has been described that suppresses the proliferation of $T_{conv}$ cells exclusively via IL-35 (Collison et al. (2010) Nature Immunology 11: 1093-1101). Both exogenously added IL-35 and $T_{reg}$ cells induce conversion of $T_{conv}$ cells to $iT_R35$ in vitro, and in vivo, under inflammatory conditions. Given that their mode of suppression is by way of IL-35, they represent a perfect tool for determining cell-mediated suppression via IL-35. Therefore, it was assessed whether $iT_R35$ suppressed the proliferation of each of the receptor deficient $T_{conv}$ cells. While $iT_R35$ suppressed wild type, Il27ra$^{-/-}$ and Il12rb1$^{-/-}$ $T_{conv}$ cells equally well, $T_{conv}$ cells that lacked expression of either IL12Rβ2 or gp130 were partially resistant and cells that lacked both IL12Rβ2 and gp130 were completely resistant to $iT_R35$ mediated suppression (data not shown). Moreover, neutralizing mAb to IL-35, but not an isotype control, completely blocked the suppressive capacity of $iT_R35$ of wild-type $T_{conv}$ cells.

IL35R-Deficient $T_{conv}$ Cells are Resistant to IL-35 Mediated Suppression In Vivo.

Figure 2A:
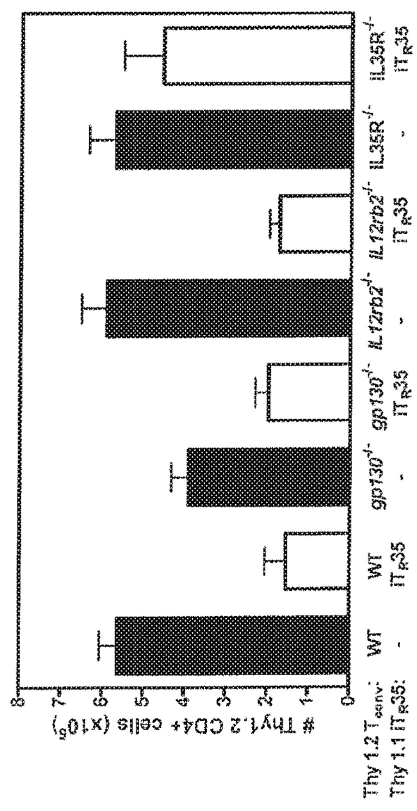
FIG. 2A demonstrates that IL35R deficient $T_{conv}$ are resistant to IL-35 mediated suppression in vivo. Homeostatic expansion was monitored by i.v. injection of Thy1.2$^{+}$ $T_{conv}$, cells from wild-type (C57BL/6), gp130$^{\Delta T}$ (gp130 deficient in T cells), Il12rb2$^{-/-}$ or IL35R$^{\Delta T}$ (gp130$^{\Delta T}$/Il12rb2$^{-/-}$) mice alone or with Thy1.1$^{+}$ i$T_{R}$35 cells (as regulatory cells) into Rag1$^{-/-}$ mice. Seven days after transfer, splenic T cell numbers were determined by flow cytometry.

In the absence of their respective cytokine signaling receptor chains, in vivo cellular effects of IL-12 and IL-27 are completely abolished. Therefore, it was determined whether loss of the IL35R in vivo renders T cells refractory to IL35-mediated suppression. Given that IL-35 is central to the suppression mediated by $iT_R35$, $iT_R35$ was utilized in two different in vivo models to address this question. First, $iT_R35$ can control the homeostatic expansion of $T_{conv}$ cells in the lymphopenic environment of the recombination activating gene-1 (Rag1)$^{-/-}$ mouse. Therefore, purified wild-type, gp130$^{\Delta T}$, Il27ra$^{-/-}$, Il12rb1$^{-/-}$, Il12rb2$^{-/-}$ or IL35R$^{\Delta T}$ Thy1.2$^+$ $T_{conv}$ cells, either alone or in the presence of Thy1.1$^+$ $iT_R35$ cells were adoptively transferred into Rag1$^{-/-}$ mice. Seven days post transfer, suppression of $T_{conv}$ cell expansion was monitored by determining the Thy1.2$^+$ $T_{conv}$ cell numbers. $iT_R35$ cells significantly limited the proliferation of wild-type, gp130$^{\Delta T}$, Il27ra$^{-/-}$, Il12rb1$^{-/-}$ and Il12rb2$^{-/-}$ Thy1.2$^+$ $T_{conv}$ cells. However, $iT_R35$ cells failed to block the expansion of IL35R$^{\Delta T}$ Thy1.1$^+$ $T_{conv}$ cells (FIG. 2A). In the absence of only one receptor chain, in vivo biological activity of both IL-12 and IL-27 is lost, it appears that IL-35 signaling in vivo is abrogated only by loss of both IL12Rβ2 and gp130 expression.

Figure 2B:
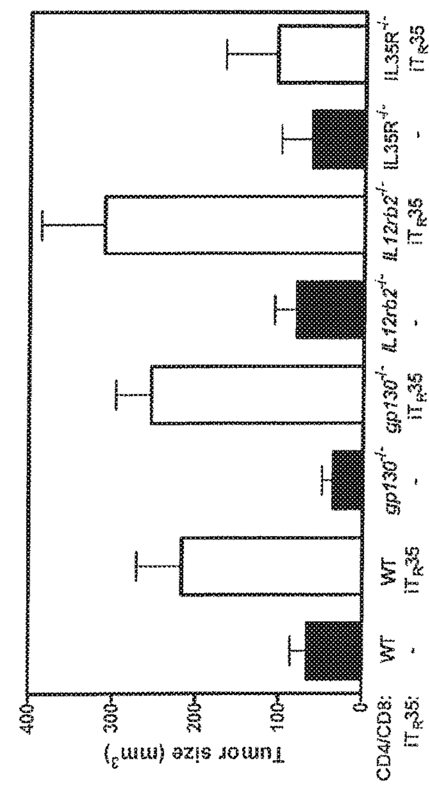
FIG. 2B demonstrates that IL35R deficient $T_{conv}$ are resistant to IL-35 mediated suppression in vivo. Rag1$^{-/-}$ mice received CD4$^{+}$ and CD8$^{+}$ T cells from wild-type (C57BL/6), gp130$^{\Delta T}$, Il12rb2$^{-/-}$ or IL35R$^{\Delta T}$ mice alone or with i$T_{R}$35 cells via the tail vein on day −1 of the experiment. On day 0, all were injected with 120,000 B16 cells i.d. in the right flank. Tumor diameter was measured daily for 14 days and is reported as mm$^{3}$. Data represent the mean±SEM of 5-12 mice per group.

Second, it was previously shown that, like natural $T_{regs}$, $iT_R35$ can block the anti-tumor CD8$^+$ T cell response against B16 melanoma. Wild-type, gp130$^{\Delta T}$, Il27ra$^{-/-}$, Il12rb2$^{-/-}$ or IL35R$^{\Delta T}$ CD4$^+$ and CD8$^+$ T cells, either alone or in the presence of $iT_R35$ cells were adoptively transferred into Rag1$^{-/-}$ mice. The following day, mice were inoculated intradermally with B16 melanoma cells and tumor size was monitored daily and reported after 14 days. In the absence of $iT_R35$, tumor burden was similar between mice receiving all CD4$^+$ and CD8$^+$ T cells, regardless of genotype (FIG. 2B). Tumor size was exacerbated in mice receiving $iT_R35$ cells in combination with wild-type, gp130$^{\Delta T}$, Il27ra$^{-/-}$, Il12rb1$^{-/-}$, and Il12rb2$^{-/-}$ CD4$^+$ and CD8$^+$ T cells. However, IL35R$^{\Delta T}$ recipients were completely resistant to $iT_R35$ mediated prevention of tumor immunity. Collectively, these data clearly demonstrate that IL35R$^{\Delta T}$ cells are resistant to IL-35 mediated suppression in vivo.

IL-35 Signals Through STAT1 and STAT4

Given that IL12Rβ2 and gp130 constitute the IL-35 receptor, it was hypothesized that the IL-35 signaling pathway might also overlap with that of other cytokines that utilize these receptor chains. $T_{conv}$ cells were activated in the presence of $T_{reg}$ at a 4:1 ratio (responder:suppressor) for 72 hours. RNA was extracted and cDNA generated from resting or activated $T_{conv}$ cells or from suppressed $T_{conv}$ cells from $T_{conv}$:$T_{reg}$ co-cultures (resorted based on differential Thy1 markers). Relative gp130, Il27ra, Il12rb1 and Il12rb2 mRNA expression was determined. Consistent with previous reports ref, IL-12 treatment of $T_{conv}$ cells resulted in phosphorylation of STAT4 and IL-27 signaling induced STAT1 and STAT3 phosphorylation (data not shown). Interestingly, wild-type $T_{conv}$ cells, which are responsive to IL-35 mediated suppression, demonstrated phosphorylation of both STAT1 and STAT4, but no activation of either STAT3 or STAT5. Moreover, no induction of p-STAT1 or p-STAT4 was seen in $T_{conv}$ cells that lack the IL-35 receptor (Il12rb2$^{-/-}$×gp130$^{\Delta T}$ $T_{conv}$, hence forth referred to as IL35R$^{\Delta T}$) (data not shown). To better determine the kinetics of STAT phosphorylation in response to IL-35 treatment, $T_{conv}$ cells were activated for 24 hours with anti-CD3+anti-CD28 coated beads and treated with IL-35 for indicated times. Western blot analysis demonstrated that p-STAT1 was the most dramatic, with maximal phosphorylation evident at 30 minutes. Similar to STAT3 and STAT5, STAT4 phosphorylation was less pronounced, but was sustained over the course of time analyzed. To determine which STATs were most critical to IL-35 signaling, $T_{conv}$ cells that lack STAT1, STAT3, or STAT4 were utilized. Whereas IL-35 can suppress the proliferation of Stat3$^{-/-}$ $T_{conv}$ cells to a degree similar to that seen in wild-type $T_{conv}$ cells, suppression of Stat1$^{-/-}$ and Stat4$^{-/-}$ $T_{conv}$ cells was reduced (data not shown). Similarly, $T_{reg}$-mediated suppression of both Stat1$^{-/-}$ and Stat4$^{-/-}$ $T_{conv}$ cells was impaired (data not shown). Reduced signaling in Stat1$^{-/-}$ and Stat4$^{-/-}$ $T_{conv}$ cells is not due to lack of receptor expression as mRNA expression of receptor chains is similar in Stat1$^{-/-}$, Stat4$^{1}$ and wild-type $T_{conv}$ cells (data not shown). Collectively, these data suggest that STAT1 and STAT4 are critical for IL-35 mediated signal transduction.

IL-35 is a Target of the IL-35 Signaling Pathway.

Figure 3A:
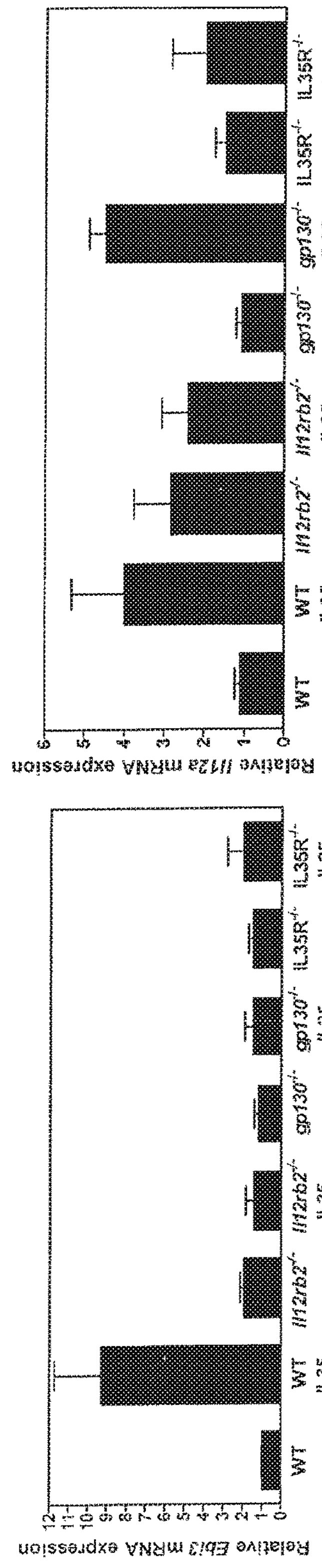
FIG. 3A demonstrates that IL35 is a target of the IL35 signaling pathway. $T_{conv}$ purified by FACS from wild-type (C57BL/6), gp130$^{\Delta T}$ (gp130 deficient in T cells), Il12rb2$^{-/-}$ or IL35R$^{\Delta T}$ (gp130$^{\Delta T}$/Il12rb2$^{-1}$) mice were activated with anti-CD3-+anti-CD28-coated latex beads for 18 hours in the presence of IL-35. RNA was extracted, cDNA generated and qPCR performed. Relative Ebi3 (left panel) and Il12a (right panel) mRNA expression.
Figure 3B:
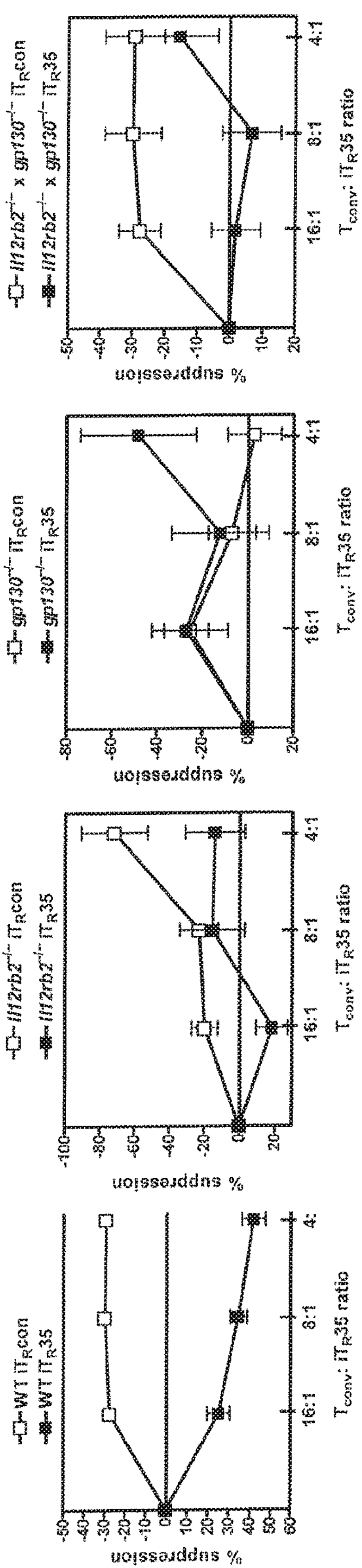
FIG. 3B demonstrates that IL35 is a target of the IL35 signaling pathway. $T_{conv}$ from wild-type (C57BL/6), gp130$^{\Delta T,\ Il}$12rb2$^{-/-}$ or IL35R$^{\Delta T}$ mice were activated in the presence of IL-35 or control protein at 25% of total culture volume, for 72 hours to generate $iT_R35$ or $iT_Rcon$ cells, respectively. Cells were re-purified and mixed at indicated ratios ($T_{conv}$:suppressor) and proliferation was determined by [$^3$H]-thymidine incorporation. Counts per minute of $T_{conv}$ cells activated alone were 29,000-48,000 (b). Data represent the mean±SEM of 3-5 independent experiments.

It has been previously shown that IL-35 can convert proliferative, IL35 $T_{conv}$ cells into hypo-responsive, strongly suppressive $iT_R35$ which express and mediate suppression via IL-35 (Collison et al. (2010) Nature Immunology 11: 1093-1101). Activation of wild-type $T_{conv}$ in the presence of IL-35 significantly upregulated Ebi3 and Il12a mRNA, the two components of IL-35 (Ebi3 and p35, respectively). Interestingly, gp130$^{\Delta T}$, Il12rb2$^{-/-}$ and IL35R$^{\Delta T}$ $T_{conv}$ cells are all resistant to induction of Ebi3 expression (FIG. 3A). However, gp130$^{\Delta T}$ $T_{conv}$ cells retain the ability to upregulate Il12a expression in response to IL-35 treatment, suggesting that p35 expression may be downstream of IL12Rβ2 signaling. Induction of IL-35 expression in response to IL-35 treatment is critical for conversion of $T_{conv}$ cells into $iT_R35$. Therefore, the ability of receptor deficient mice to be converted into $iT_R35$ was assessed. To determine whether IL-35 treated $T_{conv}$ cells had acquired regulatory capacity, they were co-cultured as suppressors with freshly purified responder $T_{conv}$ cells (FIG. 3B). $T_{c0}$, cells treated with control protein, regardless of genotype, were incapable of suppressing responder $T_{conv}$ cell proliferation. Furthermore, wild-type, but not gp130$^{\Delta T, Il}$12rb2$^{-/-}$ or IL35R$^{\Delta T}$ $T_{conv}$ cells were capable of suppressing $T_{conv}$ cell proliferation. In addition, both Stat1$^{-/-}$, Stat4$^{-/-}$ $T_{conv}$ cells fail to upregulate expression of Ebi3 and Il12a to the same degree as wild-type $T_{conv}$ cells (data not shown). Moreover, early induction of Ebi3 and Il12a mRNA expression, which peak at 3 hours and 1 hour, respectively, suggest that IL-35 is a direct target of IL-35 signaling (data not shown). Together, these results suggest that cells that lack the IL-35 receptor or signaling components are unable to induce IL-35 expression.

DISCUSSION

Important similarities and interesting differences between IL-12, IL-27 and IL-35 signaling have been illuminated by this study. Not surprisingly, the IL-35 receptor and signaling pathway overlap with that of IL-12 and IL-27. However, unlike its siblings, IL-35 appears to be able to signal, in part, through each of the receptor chains, IL-12Rβ2 and gp130. This is likely due to the fact that each of these chains is the signal transducing subunit of their respective cytokine receptors. In addition, like IL-27, IL-35 signals primarily through two different STAT proteins, STAT1 and STAT4. However, STAT3 appears dispensable for IL-35 signaling, an interesting observation given its importance for IL-27 signaling, which is downstream of gp130 engagement. In addition, STAT1/STAT3 heterodimers have been previously described yet there is no precedent for STAT1/STAT 4 heterodimerization.

The expression pattern of the IL-35 receptor also provides insight into potential IL-35 target cell types. While gp130 is fairly ubiquitously expressed, both IL-12R chains are expressed mainly by activated T cells and NK cells. In T cells, the expression of IL-12Rβ2 is confined to Th1 cells, and its expression correlates with responsiveness to IL-12 and presumably IL-35. Expression of IL-12Rβ2 has also been shown on other cell types, such as dendritic cells which would vastly affect the scope of IL-35 bioactivity in the immune system. IL-12Rβ2 is undetectable on most resting T cells, but can be rapidly upregulated by exposure to IL-12, IL-27, IFN-y, tumor-necrosis factor (TNF) and co-stimulation through CD28. Thus, IL35 might have biological effects on a variety of cellular targets and under a variety of disease conditions.

Since IL-35 appears to utilize receptor chains and STATs that are similar to those used by other IL-12 family members, another important question is how a T cell can translate potentially similar signals into such distinct biological outcomes. Given the opposing activities of IL-35 and IL-12, IL-23, and IL-27, it is possible that different kinetics, binding affinities, or potentially as yet unidentified heterodimerization patterns may differentiate the signaling pathways in such a way to mediate such diverse biological consequences.

TABLE 1

Summary of SEQ ID NOS

| SEQ ID NO | Description | Type of sequence |
|---|---|---|
| 1 | gp130 | Full length cDNA |
| 2 | gp130 | DNA coding region |
| 3 | gp130 | Amino acid |
| 4 | IL12Rβ2 | Full length cDNA |
| 5 | IL12Rβ2 | DNA coding region |
| 6 | IL12Rβ2 | Amino acid |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide or mixture of polynucleotides, comprising:

(a) a first polynucleotide sequence encoding the extracellular domain of the polypeptide sequence set forth in SEQ ID NO:3, wherein the first polynucleotide is operably linked to a first heterologous regulatory sequence; and (b) a second polynucleotide sequence encoding the extracellular domain of the polypeptide sequence set forth in SEQ ID NO:6, wherein the second polynucleotide is operably linked to a second heterologous regulatory sequence.

2. An isolated cell comprising the polynucleotide or mixture of polynucleotides of claim 1.

3. An isolated expression construct or mixture of expression constructs comprising the polynucleotide or mixture of polynucleotides of claim 1.

4. The polynucleotide or mixture of polynucleotides of claim 1, wherein each of the first and second heterologous regulatory sequences are promoters.

5. The polynucleotide or mixture of polynucleotides of claim 4, wherein each of the first and second promoters are the same promoter.

6. The polynucleotide or mixture of polynucleotides of claim 4, wherein each of the first and second promoters are distinct promoters.

7. The polynucleotide or mixture of polynucleotides of claim 1, wherein the first polynucleotide sequence encodes the polypeptide sequence set forth in SEQ ID NO:3.

8. The polynucleotide or mixture of polynucleotides of claim 1, wherein the second polynucleotide sequence encodes the polypeptide sequence set forth in SEQ ID NO:6.

9. The polynucleotide or mixture of polynucleotides of claim 1, wherein the first polynucleotide sequence encodes the polypeptide sequence set forth in SEQ ID NO:3; and the second polynucleotide sequence encodes the polypeptide sequence set forth in SEQ ID NO:6.

10. The polynucleotide or mixture of polynucleotides of claim 4, wherein one or more of the promoters are constitutive.

11. The polynucleotide or mixture of polynucleotides of claim 4, wherein one or more of the promoters are inducible.

12. The cell of claim 2, wherein the cell is eukaryotic.

13. The cell of claim 2, wherein the cell is mammalian.

14. An isolated vector or set of vectors comprising the polynucleotide or mixture of polynucleotides of claim 1.

15. The cell of claim 2, wherein the cell is stably transformed with the polynucleotide or mixture of polynucleotides.

* * * * *

SEQUENCE LISTING

<160> NUMBER OF SEQ ID NOS: 6

<210> SEQ ID NO 1
<211> LENGTH: 3242
<212> TYPE: DNA
<213> ORGANISM: Homo sapiens
<220> FEATURE:
<221> NAME/KEY: CDS
<222> LOCATION: (256)...(3010)

```
<220> FEATURE:
<221> NAME/KEY: misc_feature
<222> LOCATION: (0)...(0)
<223> OTHER INFORMATION: cDNA for gp130
<300> PUBLICATION INFORMATION:
<308> DATABASE ACCESSION NUMBER: GenBank Accession No. NM_002184.2
<309> DATABASE ENTRY DATE: 2010-05-23

<400> SEQUENCE: 1

gagcagccaa aaggcccgcg gagtcgcgct gggccgcccc ggcgcagctg aaccgggggc     60

cgcgcctgcc aggccgacgg gtctggccca gcctggcgcc aaggggttcg tgcgctgtgg    120

agacgcggag ggtcgaggcg gcgcggcctg agtgaaaccc aatggaaaaa gcatgacatt    180

tagaagtaga agacttagct tcaaatccct actccttcac ttactaattt tgtgatttgg    240

aaatatccgc gcaag atg ttg acg ttg cag act tgg cta gtg caa gcc ttg     291
                 Met Leu Thr Leu Gln Thr Trp Leu Val Gln Ala Leu
                  1               5                  10

ttt att ttc ctc acc act gaa tct aca ggt gaa ctt cta gat cca tgt      339
Phe Ile Phe Leu Thr Thr Glu Ser Thr Gly Glu Leu Leu Asp Pro Cys
         15                  20                  25

ggt tat atc agt cct gaa tct cca gtt gta caa ctt cat tct aat ttc      387
Gly Tyr Ile Ser Pro Glu Ser Pro Val Val Gln Leu His Ser Asn Phe
     30                  35                  40

act gca gtt tgt gtg cta aag gaa aaa tgt atg gat tat ttt cat gta      435
Thr Ala Val Cys Val Leu Lys Glu Lys Cys Met Asp Tyr Phe His Val
 45                  50                  55                  60

aat gct aat tac att gtc tgg aaa aca aac cat ttt act att cct aag      483
Asn Ala Asn Tyr Ile Val Trp Lys Thr Asn His Phe Thr Ile Pro Lys
                 65                  70                  75

gag caa tat act atc ata aac aga aca gca tcc agt gtc acc ttt aca      531
Glu Gln Tyr Thr Ile Ile Asn Arg Thr Ala Ser Ser Val Thr Phe Thr
             80                  85                  90

gat ata gct tca tta aat att cag ctc act tgc aac att ctt aca ttc      579
Asp Ile Ala Ser Leu Asn Ile Gln Leu Thr Cys Asn Ile Leu Thr Phe
         95                 100                 105

gga cag ctt gaa cag aat gtt tat gga atc aca ata att tca ggc ttg      627
Gly Gln Leu Glu Gln Asn Val Tyr Gly Ile Thr Ile Ile Ser Gly Leu
    110                 115                 120

cct cca gaa aaa cct aaa aat ttg agt tgc att gtg aac gag ggg aag      675
Pro Pro Glu Lys Pro Lys Asn Leu Ser Cys Ile Val Asn Glu Gly Lys
125                 130                 135                 140

aaa atg agg tgt gag tgg gat ggt gga agg gaa aca cac ttg gag aca      723
Lys Met Arg Cys Glu Trp Asp Gly Gly Arg Glu Thr His Leu Glu Thr
                145                 150                 155

aac ttc act tta aaa tct gaa tgg gca aca cac aag ttt gct gat tgc      771
Asn Phe Thr Leu Lys Ser Glu Trp Ala Thr His Lys Phe Ala Asp Cys
            160                 165                 170

aaa gca aaa cgt gac acc ccc acc tca tgc act gtt gat tat tct act      819
Lys Ala Lys Arg Asp Thr Pro Thr Ser Cys Thr Val Asp Tyr Ser Thr
        175                 180                 185

gtg tat ttt gtc aac att gaa gtc tgg gta gaa gca gag aat gcc ctt      867
Val Tyr Phe Val Asn Ile Glu Val Trp Val Glu Ala Glu Asn Ala Leu
    190                 195                 200

ggg aag gtt aca tca gat cat atc aat ttt gat cct gta tat aaa gtg      915
Gly Lys Val Thr Ser Asp His Ile Asn Phe Asp Pro Val Tyr Lys Val
205                 210                 215                 220

aag ccc aat ccg cca cat aat tta tca gtg atc aac tca gag gaa ctg      963
Lys Pro Asn Pro Pro His Asn Leu Ser Val Ile Asn Ser Glu Glu Leu
                225                 230                 235
```

-continued

```
tct agt atc tta aaa ttg aca tgg acc aac cca agt att aag agt gtt      1011
Ser Ser Ile Leu Lys Leu Thr Trp Thr Asn Pro Ser Ile Lys Ser Val
            240                 245                 250

ata ata cta aaa tat aac att caa tat agg acc aaa gat gcc tca act      1059
Ile Ile Leu Lys Tyr Asn Ile Gln Tyr Arg Thr Lys Asp Ala Ser Thr
        255                 260                 265

tgg agc cag att cct cct gaa gac aca gca tcc acc cga tct tca ttc      1107
Trp Ser Gln Ile Pro Pro Glu Asp Thr Ala Ser Thr Arg Ser Ser Phe
    270                 275                 280

act gtc caa gac ctt aaa cct ttt aca gaa tat gtg ttt agg att cgc      1155
Thr Val Gln Asp Leu Lys Pro Phe Thr Glu Tyr Val Phe Arg Ile Arg
285                 290                 295                 300

tgt atg aag gaa gat ggt aag gga tac tgg agt gac tgg agt gaa gaa      1203
Cys Met Lys Glu Asp Gly Lys Gly Tyr Trp Ser Asp Trp Ser Glu Glu
                305                 310                 315

gca agt ggg atc acc tat gaa gat aga cca tct aaa gca cca agt ttc      1251
Ala Ser Gly Ile Thr Tyr Glu Asp Arg Pro Ser Lys Ala Pro Ser Phe
            320                 325                 330

tgg tat aaa ata gat cca tcc cat act caa ggc tac aga act gta caa      1299
Trp Tyr Lys Ile Asp Pro Ser His Thr Gln Gly Tyr Arg Thr Val Gln
        335                 340                 345

ctc gtg tgg aag aca ttg cct cct ttt gaa gcc aat gga aaa atc ttg      1347
Leu Val Trp Lys Thr Leu Pro Pro Phe Glu Ala Asn Gly Lys Ile Leu
    350                 355                 360

gat tat gaa gtg act ctc aca aga tgg aaa tca cat tta caa aat tac      1395
Asp Tyr Glu Val Thr Leu Thr Arg Trp Lys Ser His Leu Gln Asn Tyr
365                 370                 375                 380

aca gtt aat gcc aca aaa ctg aca gta aat ctc aca aat gat cgc tat      1443
Thr Val Asn Ala Thr Lys Leu Thr Val Asn Leu Thr Asn Asp Arg Tyr
                385                 390                 395

cta gca acc cta aca gta aga aat ctt gtt ggc aaa tca gat gca gct      1491
Leu Ala Thr Leu Thr Val Arg Asn Leu Val Gly Lys Ser Asp Ala Ala
            400                 405                 410

gtt tta act atc cct gcc tgt gac ttt caa gct act cac cct gta atg      1539
Val Leu Thr Ile Pro Ala Cys Asp Phe Gln Ala Thr His Pro Val Met
        415                 420                 425

gat ctt aaa gca ttc ccc aaa gat aac atg ctt tgg gtg gaa tgg act      1587
Asp Leu Lys Ala Phe Pro Lys Asp Asn Met Leu Trp Val Glu Trp Thr
    430                 435                 440

act cca agg gaa tct gta aag aaa tat ata ctt gag tgg tgt gtg tta      1635
Thr Pro Arg Glu Ser Val Lys Lys Tyr Ile Leu Glu Trp Cys Val Leu
445                 450                 455                 460

tca gat aaa gca ccc tgt atc aca gac tgg caa caa gaa gat ggt acc      1683
Ser Asp Lys Ala Pro Cys Ile Thr Asp Trp Gln Gln Glu Asp Gly Thr
                465                 470                 475

gtg cat cgc acc tat tta aga ggg aac tta gca gag agc aaa tgc tat      1731
Val His Arg Thr Tyr Leu Arg Gly Asn Leu Ala Glu Ser Lys Cys Tyr
            480                 485                 490

ttg ata aca gtt act cca gta tat gct gat gga cca gga agc cct gaa      1779
Leu Ile Thr Val Thr Pro Val Tyr Ala Asp Gly Pro Gly Ser Pro Glu
        495                 500                 505

tcc ata aag gca tac ctt aaa caa gct cca cct tcc aaa gga cct act      1827
Ser Ile Lys Ala Tyr Leu Lys Gln Ala Pro Pro Ser Lys Gly Pro Thr
    510                 515                 520

gtt cgg aca aaa aaa gta ggg aaa aac gaa gct gtc tta gag tgg gac      1875
Val Arg Thr Lys Lys Val Gly Lys Asn Glu Ala Val Leu Glu Trp Asp
525                 530                 535                 540

caa ctt cct gtt gat gtt cag aat gga ttt atc aga aat tat act ata      1923
Gln Leu Pro Val Asp Val Gln Asn Gly Phe Ile Arg Asn Tyr Thr Ile
                545                 550                 555
```

```
ttt tat aga acc atc att gga aat gaa act gct gtg aat gtg gat tct      1971
Phe Tyr Arg Thr Ile Ile Gly Asn Glu Thr Ala Val Asn Val Asp Ser
            560                 565                 570

tcc cac aca gaa tat aca ttg tcc tct ttg act agt gac aca ttg tac      2019
Ser His Thr Glu Tyr Thr Leu Ser Ser Leu Thr Ser Asp Thr Leu Tyr
        575                 580                 585

atg gta cga atg gca gca tac aca gat gaa ggt ggg aag gat ggt cca      2067
Met Val Arg Met Ala Ala Tyr Thr Asp Glu Gly Gly Lys Asp Gly Pro
    590                 595                 600

gaa ttc act ttt act acc cca aag ttt gct caa gga gaa att gaa gcc      2115
Glu Phe Thr Phe Thr Thr Pro Lys Phe Ala Gln Gly Glu Ile Glu Ala
605                 610                 615                 620

ata gtc gtg cct gtt tgc tta gca ttc cta ttg aca act ctt ctg gga      2163
Ile Val Val Pro Val Cys Leu Ala Phe Leu Leu Thr Thr Leu Leu Gly
                625                 630                 635

gtg ctg ttc tgc ttt aat aag cga gac cta att aaa aaa cac atc tgg      2211
Val Leu Phe Cys Phe Asn Lys Arg Asp Leu Ile Lys Lys His Ile Trp
            640                 645                 650

cct aat gtt cca gat cct tca aag agt cat att gcc cag tgg tca cct      2259
Pro Asn Val Pro Asp Pro Ser Lys Ser His Ile Ala Gln Trp Ser Pro
        655                 660                 665

cac act cct cca agg cac aat ttt aat tca aaa gat caa atg tat tca      2307
His Thr Pro Pro Arg His Asn Phe Asn Ser Lys Asp Gln Met Tyr Ser
    670                 675                 680

gat ggc aat ttc act gat gta agt gtt gtg gaa ata gaa gca aat gac      2355
Asp Gly Asn Phe Thr Asp Val Ser Val Val Glu Ile Glu Ala Asn Asp
685                 690                 695                 700

aaa aag cct ttt cca gaa gat ctg aaa tca ttg gac ctg ttc aaa aag      2403
Lys Lys Pro Phe Pro Glu Asp Leu Lys Ser Leu Asp Leu Phe Lys Lys
                705                 710                 715

gaa aaa att aat act gaa gga cac agc agt ggt att ggg ggg tct tca      2451
Glu Lys Ile Asn Thr Glu Gly His Ser Ser Gly Ile Gly Gly Ser Ser
            720                 725                 730

tgc atg tca tct tct agg cca agc att tct agc agt gat gaa aat gaa      2499
Cys Met Ser Ser Ser Arg Pro Ser Ile Ser Ser Ser Asp Glu Asn Glu
        735                 740                 745

tct tca caa aac act tcg agc act gtc cag tat tct acc gtg gta cac      2547
Ser Ser Gln Asn Thr Ser Ser Thr Val Gln Tyr Ser Thr Val Val His
    750                 755                 760

agt ggc tac aga cac caa gtt ccg tca gtc caa gtc ttc tca aga tcc      2595
Ser Gly Tyr Arg His Gln Val Pro Ser Val Gln Val Phe Ser Arg Ser
765                 770                 775                 780

gag tct acc cag ccc ttg tta gat tca gag gag cgg cca gaa gat cta      2643
Glu Ser Thr Gln Pro Leu Leu Asp Ser Glu Glu Arg Pro Glu Asp Leu
                785                 790                 795

caa tta gta gat cat gta gat ggc ggt gat ggt att ttg ccc agg caa      2691
Gln Leu Val Asp His Val Asp Gly Gly Asp Gly Ile Leu Pro Arg Gln
            800                 805                 810

cag tac ttc aaa cag aac tgc agt cag cat gaa tcc agt cca gat att      2739
Gln Tyr Phe Lys Gln Asn Cys Ser Gln His Glu Ser Ser Pro Asp Ile
        815                 820                 825

tca cat ttt gaa agg tca aag caa gtt tca tca gtc aat gag gaa gat      2787
Ser His Phe Glu Arg Ser Lys Gln Val Ser Ser Val Asn Glu Glu Asp
    830                 835                 840

ttt gtt aga ctt aaa cag cag att tca gat cat att tca caa tcc tgt      2835
Phe Val Arg Leu Lys Gln Gln Ile Ser Asp His Ile Ser Gln Ser Cys
845                 850                 855                 860

gga tct ggg caa atg aaa atg ttt cag gaa gtt tct gca gca gat gct      2883
Gly Ser Gly Gln Met Lys Met Phe Gln Glu Val Ser Ala Ala Asp Ala
                865                 870                 875
```

```
ttt ggt cca ggt act gag gga caa gta gaa aga ttt gaa aca gtt ggc     2931
Phe Gly Pro Gly Thr Glu Gly Gln Val Glu Arg Phe Glu Thr Val Gly
            880                 885                 890

atg gag gct gcg act gat gaa ggc atg cct aaa agt tac tta cca cag     2979
Met Glu Ala Ala Thr Asp Glu Gly Met Pro Lys Ser Tyr Leu Pro Gln
        895                 900                 905

act gta cgg caa ggc ggc tac atg cct cag t gaaggactag tagttcctgc     3030
Thr Val Arg Gln Gly Gly Tyr Met Pro Gln
    910                 915

tacaacttca gcagtaccta taaagtaaag ctaaaatgat tttatctgtg aattcagatt   3090

ttaaaaagtc ttcactctct gaagatgatc atttgccctt aaggacaaaa atgaactgaa   3150

gtttcacatg agctatttcc attccagaat atctgggatt ctactttaag cactacataa   3210

actgacttta tcctcagaaa aaaaaaaaaa aa                                 3242


<210> SEQ ID NO 2
<211> LENGTH: 2757
<212> TYPE: DNA
<213> ORGANISM: Homo sapiens
<220> FEATURE:
<221> NAME/KEY: misc_feature
<222> LOCATION: (0)...(0)
<223> OTHER INFORMATION: gp130 coding region
<220> FEATURE:
<221> NAME/KEY: CDS
<222> LOCATION: (1)...(2757)

<400> SEQUENCE: 2

atg ttg acg ttg cag act tgg cta gtg caa gcc ttg ttt att ttc ctc       48
Met Leu Thr Leu Gln Thr Trp Leu Val Gln Ala Leu Phe Ile Phe Leu
 1               5                  10                  15

acc act gaa tct aca ggt gaa ctt cta gat cca tgt ggt tat atc agt       96
Thr Thr Glu Ser Thr Gly Glu Leu Leu Asp Pro Cys Gly Tyr Ile Ser
            20                  25                  30

cct gaa tct cca gtt gta caa ctt cat tct aat ttc act gca gtt tgt      144
Pro Glu Ser Pro Val Val Gln Leu His Ser Asn Phe Thr Ala Val Cys
        35                  40                  45

gtg cta aag gaa aaa tgt atg gat tat ttt cat gta aat gct aat tac      192
Val Leu Lys Glu Lys Cys Met Asp Tyr Phe His Val Asn Ala Asn Tyr
     50                  55                  60

att gtc tgg aaa aca aac cat ttt act att cct aag gag caa tat act      240
Ile Val Trp Lys Thr Asn His Phe Thr Ile Pro Lys Glu Gln Tyr Thr
 65                  70                  75                  80

atc ata aac aga aca gca tcc agt gtc acc ttt aca gat ata gct tca      288
Ile Ile Asn Arg Thr Ala Ser Ser Val Thr Phe Thr Asp Ile Ala Ser
                85                  90                  95

tta aat att cag ctc act tgc aac att ctt aca ttc gga cag ctt gaa      336
Leu Asn Ile Gln Leu Thr Cys Asn Ile Leu Thr Phe Gly Gln Leu Glu
            100                 105                 110

cag aat gtt tat gga atc aca ata att tca ggc ttg cct cca gaa aaa      384
Gln Asn Val Tyr Gly Ile Thr Ile Ile Ser Gly Leu Pro Pro Glu Lys
        115                 120                 125

cct aaa aat ttg agt tgc att gtg aac gag ggg aag aaa atg agg tgt      432
Pro Lys Asn Leu Ser Cys Ile Val Asn Glu Gly Lys Lys Met Arg Cys
    130                 135                 140

gag tgg gat ggt gga agg gaa aca cac ttg gag aca aac ttc act tta      480
Glu Trp Asp Gly Gly Arg Glu Thr His Leu Glu Thr Asn Phe Thr Leu
145                 150                 155                 160

aaa tct gaa tgg gca aca cac aag ttt gct gat tgc aaa gca aaa cgt      528
Lys Ser Glu Trp Ala Thr His Lys Phe Ala Asp Cys Lys Ala Lys Arg
                165                 170                 175
```

-continued

```
gac acc ccc acc tca tgc act gtt gat tat tct act gtg tat ttt gtc      576
Asp Thr Pro Thr Ser Cys Thr Val Asp Tyr Ser Thr Val Tyr Phe Val
            180                 185                 190

aac att gaa gtc tgg gta gaa gca gag aat gcc ctt ggg aag gtt aca      624
Asn Ile Glu Val Trp Val Glu Ala Glu Asn Ala Leu Gly Lys Val Thr
        195                 200                 205

tca gat cat atc aat ttt gat cct gta tat aaa gtg aag ccc aat ccg      672
Ser Asp His Ile Asn Phe Asp Pro Val Tyr Lys Val Lys Pro Asn Pro
    210                 215                 220

cca cat aat tta tca gtg atc aac tca gag gaa ctg tct agt atc tta      720
Pro His Asn Leu Ser Val Ile Asn Ser Glu Glu Leu Ser Ser Ile Leu
225                 230                 235                 240

aaa ttg aca tgg acc aac cca agt att aag agt gtt ata ata cta aaa      768
Lys Leu Thr Trp Thr Asn Pro Ser Ile Lys Ser Val Ile Ile Leu Lys
                245                 250                 255

tat aac att caa tat agg acc aaa gat gcc tca act tgg agc cag att      816
Tyr Asn Ile Gln Tyr Arg Thr Lys Asp Ala Ser Thr Trp Ser Gln Ile
            260                 265                 270

cct cct gaa gac aca gca tcc acc cga tct tca ttc act gtc caa gac      864
Pro Pro Glu Asp Thr Ala Ser Thr Arg Ser Ser Phe Thr Val Gln Asp
        275                 280                 285

ctt aaa cct ttt aca gaa tat gtg ttt agg att cgc tgt atg aag gaa      912
Leu Lys Pro Phe Thr Glu Tyr Val Phe Arg Ile Arg Cys Met Lys Glu
    290                 295                 300

gat ggt aag gga tac tgg agt gac tgg agt gaa gaa gca agt ggg atc      960
Asp Gly Lys Gly Tyr Trp Ser Asp Trp Ser Glu Glu Ala Ser Gly Ile
305                 310                 315                 320

acc tat gaa gat aga cca tct aaa gca cca agt ttc tgg tat aaa ata     1008
Thr Tyr Glu Asp Arg Pro Ser Lys Ala Pro Ser Phe Trp Tyr Lys Ile
                325                 330                 335

gat cca tcc cat act caa ggc tac aga act gta caa ctc gtg tgg aag     1056
Asp Pro Ser His Thr Gln Gly Tyr Arg Thr Val Gln Leu Val Trp Lys
            340                 345                 350

aca ttg cct cct ttt gaa gcc aat gga aaa atc ttg gat tat gaa gtg     1104
Thr Leu Pro Pro Phe Glu Ala Asn Gly Lys Ile Leu Asp Tyr Glu Val
        355                 360                 365

act ctc aca aga tgg aaa tca cat tta caa aat tac aca gtt aat gcc     1152
Thr Leu Thr Arg Trp Lys Ser His Leu Gln Asn Tyr Thr Val Asn Ala
    370                 375                 380

aca aaa ctg aca gta aat ctc aca aat gat cgc tat cta gca acc cta     1200
Thr Lys Leu Thr Val Asn Leu Thr Asn Asp Arg Tyr Leu Ala Thr Leu
385                 390                 395                 400

aca gta aga aat ctt gtt ggc aaa tca gat gca gct gtt tta act atc     1248
Thr Val Arg Asn Leu Val Gly Lys Ser Asp Ala Ala Val Leu Thr Ile
                405                 410                 415

cct gcc tgt gac ttt caa gct act cac cct gta atg gat ctt aaa gca     1296
Pro Ala Cys Asp Phe Gln Ala Thr His Pro Val Met Asp Leu Lys Ala
            420                 425                 430

ttc ccc aaa gat aac atg ctt tgg gtg gaa tgg act act cca agg gaa     1344
Phe Pro Lys Asp Asn Met Leu Trp Val Glu Trp Thr Thr Pro Arg Glu
        435                 440                 445

tct gta aag aaa tat ata ctt gag tgg tgt gtg tta tca gat aaa gca     1392
Ser Val Lys Lys Tyr Ile Leu Glu Trp Cys Val Leu Ser Asp Lys Ala
    450                 455                 460

ccc tgt atc aca gac tgg caa caa gaa gat ggt acc gtg cat cgc acc     1440
Pro Cys Ile Thr Asp Trp Gln Gln Glu Asp Gly Thr Val His Arg Thr
465                 470                 475                 480

tat tta aga ggg aac tta gca gag agc aaa tgc tat ttg ata aca gtt     1488
Tyr Leu Arg Gly Asn Leu Ala Glu Ser Lys Cys Tyr Leu Ile Thr Val
                485                 490                 495
```

```
act cca gta tat gct gat gga cca gga agc cct gaa tcc ata aag gca      1536
Thr Pro Val Tyr Ala Asp Gly Pro Gly Ser Pro Glu Ser Ile Lys Ala
            500                 505                 510

tac ctt aaa caa gct cca cct tcc aaa gga cct act gtt cgg aca aaa      1584
Tyr Leu Lys Gln Ala Pro Pro Ser Lys Gly Pro Thr Val Arg Thr Lys
        515                 520                 525

aaa gta ggg aaa aac gaa gct gtc tta gag tgg gac caa ctt cct gtt      1632
Lys Val Gly Lys Asn Glu Ala Val Leu Glu Trp Asp Gln Leu Pro Val
    530                 535                 540

gat gtt cag aat gga ttt atc aga aat tat act ata ttt tat aga acc      1680
Asp Val Gln Asn Gly Phe Ile Arg Asn Tyr Thr Ile Phe Tyr Arg Thr
545                 550                 555                 560

atc att gga aat gaa act gct gtg aat gtg gat tct tcc cac aca gaa      1728
Ile Ile Gly Asn Glu Thr Ala Val Asn Val Asp Ser Ser His Thr Glu
                565                 570                 575

tat aca ttg tcc tct ttg act agt gac aca ttg tac atg gta cga atg      1776
Tyr Thr Leu Ser Ser Leu Thr Ser Asp Thr Leu Tyr Met Val Arg Met
            580                 585                 590

gca gca tac aca gat gaa ggt ggg aag gat ggt cca gaa ttc act ttt      1824
Ala Ala Tyr Thr Asp Glu Gly Gly Lys Asp Gly Pro Glu Phe Thr Phe
        595                 600                 605

act acc cca aag ttt gct caa gga gaa att gaa gcc ata gtc gtg cct      1872
Thr Thr Pro Lys Phe Ala Gln Gly Glu Ile Glu Ala Ile Val Val Pro
    610                 615                 620

gtt tgc tta gca ttc cta ttg aca act ctt ctg gga gtg ctg ttc tgc      1920
Val Cys Leu Ala Phe Leu Leu Thr Thr Leu Leu Gly Val Leu Phe Cys
625                 630                 635                 640

ttt aat aag cga gac cta att aaa aaa cac atc tgg cct aat gtt cca      1968
Phe Asn Lys Arg Asp Leu Ile Lys Lys His Ile Trp Pro Asn Val Pro
                645                 650                 655

gat cct tca aag agt cat att gcc cag tgg tca cct cac act cct cca      2016
Asp Pro Ser Lys Ser His Ile Ala Gln Trp Ser Pro His Thr Pro Pro
            660                 665                 670

agg cac aat ttt aat tca aaa gat caa atg tat tca gat ggc aat ttc      2064
Arg His Asn Phe Asn Ser Lys Asp Gln Met Tyr Ser Asp Gly Asn Phe
        675                 680                 685

act gat gta agt gtt gtg gaa ata gaa gca aat gac aaa aag cct ttt      2112
Thr Asp Val Ser Val Val Glu Ile Glu Ala Asn Asp Lys Lys Pro Phe
    690                 695                 700

cca gaa gat ctg aaa tca ttg gac ctg ttc aaa aag gaa aaa att aat      2160
Pro Glu Asp Leu Lys Ser Leu Asp Leu Phe Lys Lys Glu Lys Ile Asn
705                 710                 715                 720

act gaa gga cac agc agt ggt att ggg ggg tct tca tgc atg tca tct      2208
Thr Glu Gly His Ser Ser Gly Ile Gly Gly Ser Ser Cys Met Ser Ser
                725                 730                 735

tct agg cca agc att tct agc agt gat gaa aat gaa tct tca caa aac      2256
Ser Arg Pro Ser Ile Ser Ser Ser Asp Glu Asn Glu Ser Ser Gln Asn
            740                 745                 750

act tcg agc act gtc cag tat tct acc gtg gta cac agt ggc tac aga      2304
Thr Ser Ser Thr Val Gln Tyr Ser Thr Val Val His Ser Gly Tyr Arg
        755                 760                 765

cac caa gtt ccg tca gtc caa gtc ttc tca aga tcc gag tct acc cag      2352
His Gln Val Pro Ser Val Gln Val Phe Ser Arg Ser Glu Ser Thr Gln
    770                 775                 780

ccc ttg tta gat tca gag gag cgg cca gaa gat cta caa tta gta gat      2400
Pro Leu Leu Asp Ser Glu Glu Arg Pro Glu Asp Leu Gln Leu Val Asp
785                 790                 795                 800

cat gta gat ggc ggt gat ggt att ttg ccc agg caa cag tac ttc aaa      2448
His Val Asp Gly Gly Asp Gly Ile Leu Pro Arg Gln Gln Tyr Phe Lys
                805                 810                 815
```

```
cag aac tgc agt cag cat gaa tcc agt cca gat att tca cat ttt gaa     2496
Gln Asn Cys Ser Gln His Glu Ser Ser Pro Asp Ile Ser His Phe Glu
            820                 825                 830

agg tca aag caa gtt tca tca gtc aat gag gaa gat ttt gtt aga ctt     2544
Arg Ser Lys Gln Val Ser Ser Val Asn Glu Glu Asp Phe Val Arg Leu
        835                 840                 845

aaa cag cag att tca gat cat att tca caa tcc tgt gga tct ggg caa     2592
Lys Gln Gln Ile Ser Asp His Ile Ser Gln Ser Cys Gly Ser Gly Gln
    850                 855                 860

atg aaa atg ttt cag gaa gtt tct gca gca gat gct ttt ggt cca ggt     2640
Met Lys Met Phe Gln Glu Val Ser Ala Ala Asp Ala Phe Gly Pro Gly
865                 870                 875                 880

act gag gga caa gta gaa aga ttt gaa aca gtt ggc atg gag gct gcg     2688
Thr Glu Gly Gln Val Glu Arg Phe Glu Thr Val Gly Met Glu Ala Ala
                885                 890                 895

act gat gaa ggc atg cct aaa agt tac tta cca cag act gta cgg caa     2736
Thr Asp Glu Gly Met Pro Lys Ser Tyr Leu Pro Gln Thr Val Arg Gln
            900                 905                 910

ggc ggc tac atg cct cag tga                                         2757
Gly Gly Tyr Met Pro Gln
        915


<210> SEQ ID NO 3
<211> LENGTH: 918
<212> TYPE: PRT
<213> ORGANISM: Homo Sapiens

<400> SEQUENCE: 3

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220
```

```
Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640
```

```
Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915


<210> SEQ ID NO 4
<211> LENGTH: 4040
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: cDNA for IL12RB2
<220> FEATURE:
<221> NAME/KEY: CDS
<222> LOCATION: (641)...(3229)
<300> PUBLICATION INFORMATION:
<308> DATABASE ACCESSION NUMBER: GenBank Acc No. M57230.1
<309> DATABASE ENTRY DATE: 1995-01-06

<400> SEQUENCE: 4

tgcagagcac agagaaagga catctgcgag gaaagttccc tgatggctgt caacaaagtg      60

ccacgtctct atggctgtga acgctgagca cacgatttta tcgcgcctat catatcttgg     120

tgcataaacg cacctcacct cggtcaaccc ttgctccgtc ttatgagaca ggctttatta     180

tccgcatttt atatgagggg aaactgacgg tggagagaga attatcttgc tcaaggcgac     240
```

```
acagcagagc ccacaggtgg cagaatccca cccgagcccg cttcgacccg cggggtggaa    300

accacgggcg cccgcccggc tgcgcttcca gagctgaact gagaagcgag tcctctccgc    360

cctgcggcca ccgcccagcc ccgacccccg ccccggcccg atcctcactc gccgccagct    420

ccccgcgccc accccggagt tggtggcgca gaggcgggag gcggaggcgg gagggcgggc    480

gctggcaccg ggaacgcccg agcgccggca gagagcgcgg agagcgcgac acgtgcggcc    540

cagagcaccg gggccacccg gtccccgcag gcccgggacc gcgcccgctg gcaggcgaca    600

cgtggaagaa tacggagttc tataccagag ttgattgttg atg gca cat act ttt      655
                                            Met Ala His Thr Phe
                                            1               5

aga gga tgc tca ttg gca ttt atg ttt ata atc acg tgg ctg ttg att      703
Arg Gly Cys Ser Leu Ala Phe Met Phe Ile Ile Thr Trp Leu Leu Ile
                10                  15                  20

aaa gca aaa ata gat gcg tgc aag aga ggc gat gtg act gtg aag cct      751
Lys Ala Lys Ile Asp Ala Cys Lys Arg Gly Asp Val Thr Val Lys Pro
            25                  30                  35

tcc cat gta att tta ctt gga tcc act gtc aat att aca tgc tct ttg      799
Ser His Val Ile Leu Leu Gly Ser Thr Val Asn Ile Thr Cys Ser Leu
        40                  45                  50

aag ccc aga caa ggc tgc ttt cac tat tcc aga cgt aac aag tta atc      847
Lys Pro Arg Gln Gly Cys Phe His Tyr Ser Arg Arg Asn Lys Leu Ile
    55                  60                  65

ctg tac aag ttt gac aga aga atc aat ttt cac cat ggc cac tcc ctc      895
Leu Tyr Lys Phe Asp Arg Arg Ile Asn Phe His His Gly His Ser Leu
70                  75                  80                  85

aat tct caa gtc aca ggt ctt ccc ctt ggt aca acc ttg ttt gtc tgc      943
Asn Ser Gln Val Thr Gly Leu Pro Leu Gly Thr Thr Leu Phe Val Cys
                90                  95                  100

aaa ctg gcc tgt atc aat agt gat gaa att caa ata tgt gga gca gag      991
Lys Leu Ala Cys Ile Asn Ser Asp Glu Ile Gln Ile Cys Gly Ala Glu
            105                 110                 115

atc ttc gtt ggt gtt gct cca gaa cag cct caa aat tta tcc tgc ata     1039
Ile Phe Val Gly Val Ala Pro Glu Gln Pro Gln Asn Leu Ser Cys Ile
        120                 125                 130

cag aag gga gaa cag ggg act gtg gcc tgc acc tgg gaa aga gga cga     1087
Gln Lys Gly Glu Gln Gly Thr Val Ala Cys Thr Trp Glu Arg Gly Arg
    135                 140                 145

gac acc cac tta tac act gag tat act cta cag cta agt gga cca aaa     1135
Asp Thr His Leu Tyr Thr Glu Tyr Thr Leu Gln Leu Ser Gly Pro Lys
150                 155                 160                 165

aat tta acc tgg cag aag caa tgt aaa gac att tat tgt gac tat ttg     1183
Asn Leu Thr Trp Gln Lys Gln Cys Lys Asp Ile Tyr Cys Asp Tyr Leu
                170                 175                 180

gac ttt gga atc aac ctc acc cct gaa tca cct gaa tcc aat ttc aca     1231
Asp Phe Gly Ile Asn Leu Thr Pro Glu Ser Pro Glu Ser Asn Phe Thr
            185                 190                 195

gcc aag gtt act gct gtc aat agt ctt gga agc tcc tct tca ctt cca     1279
Ala Lys Val Thr Ala Val Asn Ser Leu Gly Ser Ser Ser Ser Leu Pro
        200                 205                 210

tcc aca ttc aca ttc ttg gac ata gtg agg cct ctt cct ccg tgg gac     1327
Ser Thr Phe Thr Phe Leu Asp Ile Val Arg Pro Leu Pro Pro Trp Asp
    215                 220                 225

att aga atc aaa ttt caa aag gct tct gtg agc aga tgt acc ctt tat     1375
Ile Arg Ile Lys Phe Gln Lys Ala Ser Val Ser Arg Cys Thr Leu Tyr
230                 235                 240                 245

tgg aga gat gag gga ctg gta ctg ctt aat cga ctc aga tat cgg ccc     1423
Trp Arg Asp Glu Gly Leu Val Leu Leu Asn Arg Leu Arg Tyr Arg Pro
                250                 255                 260
```

-continued

```
agt aac agc agg ctc tgg aat atg gtt aat gtt aca aag gcc aaa gga      1471
Ser Asn Ser Arg Leu Trp Asn Met Val Asn Val Thr Lys Ala Lys Gly
            265                 270                 275

aga cat gat ttg ctg gat ctg aaa cca ttt aca gaa tat gaa ttt cag      1519
Arg His Asp Leu Leu Asp Leu Lys Pro Phe Thr Glu Tyr Glu Phe Gln
        280                 285                 290

att tcc tct aag cta cat ctt tat aag gga agt tgg agt gat tgg agt      1567
Ile Ser Ser Lys Leu His Leu Tyr Lys Gly Ser Trp Ser Asp Trp Ser
    295                 300                 305

gaa tca ttg aga gca caa aca cca gaa gaa gag cct act ggg atg tta      1615
Glu Ser Leu Arg Ala Gln Thr Pro Glu Glu Glu Pro Thr Gly Met Leu
310                 315                 320                 325

gat gtc tgg tac atg aaa cgg cac att gac tac agt aga caa cag att      1663
Asp Val Trp Tyr Met Lys Arg His Ile Asp Tyr Ser Arg Gln Gln Ile
                330                 335                 340

tct ctt ttc tgg aag aat ctg agt gtc tca gag gca aga gga aaa att      1711
Ser Leu Phe Trp Lys Asn Leu Ser Val Ser Glu Ala Arg Gly Lys Ile
            345                 350                 355

ctc cac tat cag gtg acc ttg cag gag ctg aca gga ggg aaa gcc atg      1759
Leu His Tyr Gln Val Thr Leu Gln Glu Leu Thr Gly Gly Lys Ala Met
        360                 365                 370

aca cag aac atc aca gga cac acc tcc tgg acc aca gtc att cct aga      1807
Thr Gln Asn Ile Thr Gly His Thr Ser Trp Thr Thr Val Ile Pro Arg
    375                 380                 385

acc gga aat tgg gct gtg gct gtg tct gca gca aat tca aaa ggc agt      1855
Thr Gly Asn Trp Ala Val Ala Val Ser Ala Ala Asn Ser Lys Gly Ser
390                 395                 400                 405

tct ctg ccc act cgt att aac ata atg aac ctg tgt gag gca ggg ttg      1903
Ser Leu Pro Thr Arg Ile Asn Ile Met Asn Leu Cys Glu Ala Gly Leu
                410                 415                 420

ctg gct cct cgc cag gtc tct gca aac tca gag ggc atg gac aac att      1951
Leu Ala Pro Arg Gln Val Ser Ala Asn Ser Glu Gly Met Asp Asn Ile
            425                 430                 435

ctg gtg act tgg cag cct ccc agg aaa gat ccc tct gct gtt cag gag      1999
Leu Val Thr Trp Gln Pro Pro Arg Lys Asp Pro Ser Ala Val Gln Glu
        440                 445                 450

tac gtg gtg gaa tgg aga gag ctc cat cca ggg ggt gac aca cag gtc      2047
Tyr Val Val Glu Trp Arg Glu Leu His Pro Gly Gly Asp Thr Gln Val
    455                 460                 465

cct cta aac tgg cta cgg agt cga ccc tac aat gtg tct gct ctg att      2095
Pro Leu Asn Trp Leu Arg Ser Arg Pro Tyr Asn Val Ser Ala Leu Ile
470                 475                 480                 485

tca gag aac ata aaa tcc tac atc tgt tat gaa atc cgt gtg tat gca      2143
Ser Glu Asn Ile Lys Ser Tyr Ile Cys Tyr Glu Ile Arg Val Tyr Ala
                490                 495                 500

ctc tca ggg gat caa gga gga tgc agc tcc atc ctg ggt aac tct aag      2191
Leu Ser Gly Asp Gln Gly Gly Cys Ser Ser Ile Leu Gly Asn Ser Lys
            505                 510                 515

cac aaa gca cca ctg agt ggc ccc cac att aat gcc atc aca gag gaa      2239
His Lys Ala Pro Leu Ser Gly Pro His Ile Asn Ala Ile Thr Glu Glu
        520                 525                 530

aag ggg agc att tta att tca tgg aac agc att cca gtc cag gag caa      2287
Lys Gly Ser Ile Leu Ile Ser Trp Asn Ser Ile Pro Val Gln Glu Gln
    535                 540                 545

atg ggc tgc ctc ctc cat tat agg ata tac tgg aag gaa cgg gac tcc      2335
Met Gly Cys Leu Leu His Tyr Arg Ile Tyr Trp Lys Glu Arg Asp Ser
550                 555                 560                 565

aac tcc cag cct cag ctc tgt gaa att ccc tac aga gtc tcc caa aat      2383
Asn Ser Gln Pro Gln Leu Cys Glu Ile Pro Tyr Arg Val Ser Gln Asn
                570                 575                 580
```

-continued

```
tca cat cca ata aac agc ctg cag ccc cga gtg aca tat gtc ctg tgg      2431
Ser His Pro Ile Asn Ser Leu Gln Pro Arg Val Thr Tyr Val Leu Trp
            585                 590                 595

atg aca gct ctg aca gct gct ggt gaa agt tcc cac gga aat gag agg      2479
Met Thr Ala Leu Thr Ala Ala Gly Glu Ser Ser His Gly Asn Glu Arg
        600                 605                 610

gaa ttt tgt ctg caa ggt aaa gcc aat tgg atg gcg ttt gtg gca cca      2527
Glu Phe Cys Leu Gln Gly Lys Ala Asn Trp Met Ala Phe Val Ala Pro
    615                 620                 625

agc att tgc att gct atc atc atg gtg ggc att ttc tca acg cat tac      2575
Ser Ile Cys Ile Ala Ile Ile Met Val Gly Ile Phe Ser Thr His Tyr
630                 635                 640                 645

ttc cag caa aag gtg ttt gtt ctc cta gca gcc ctc aga cct cag tgg      2623
Phe Gln Gln Lys Val Phe Val Leu Leu Ala Ala Leu Arg Pro Gln Trp
                650                 655                 660

tgt agc aga gaa att cca gat cca gca aat agc act tgc gct aag aaa      2671
Cys Ser Arg Glu Ile Pro Asp Pro Ala Asn Ser Thr Cys Ala Lys Lys
            665                 670                 675

tat ccc att gca gag gag aag aca cag ctg ccc ttg gac agg ctc ctg      2719
Tyr Pro Ile Ala Glu Glu Lys Thr Gln Leu Pro Leu Asp Arg Leu Leu
        680                 685                 690

ata gac tgg ccc acg cct gaa gat cct gaa ccg ctg gtc atc agt gaa      2767
Ile Asp Trp Pro Thr Pro Glu Asp Pro Glu Pro Leu Val Ile Ser Glu
    695                 700                 705

gtc ctt cat caa gtg acc cca gtt ttc aga cat ccc ccc tgc tcc aac      2815
Val Leu His Gln Val Thr Pro Val Phe Arg His Pro Pro Cys Ser Asn
710                 715                 720                 725

tgg cca caa agg gaa aaa gga atc caa ggt cat cag gcc tct gag aaa      2863
Trp Pro Gln Arg Glu Lys Gly Ile Gln Gly His Gln Ala Ser Glu Lys
                730                 735                 740

gac atg atg cac agt gcc tca agc cca cca cct cca aga gct ctc caa      2911
Asp Met Met His Ser Ala Ser Ser Pro Pro Pro Pro Arg Ala Leu Gln
            745                 750                 755

gct gag agc aga caa ctg gtg gat ctg tac aag gtg ctg gag agc agg      2959
Ala Glu Ser Arg Gln Leu Val Asp Leu Tyr Lys Val Leu Glu Ser Arg
        760                 765                 770

ggc tcc gac cca aag ccc gaa aac cca gcc tgt ccc tgg acg gtg ctc      3007
Gly Ser Asp Pro Lys Pro Glu Asn Pro Ala Cys Pro Trp Thr Val Leu
    775                 780                 785

cca gca ggt gac ctt ccc acc cat gat ggc tac tta ccc tcc aac ata      3055
Pro Ala Gly Asp Leu Pro Thr His Asp Gly Tyr Leu Pro Ser Asn Ile
790                 795                 800                 805

gat gac ctc ccc tca cat gag gca cct ctc gct gac tct ctg gaa gaa      3103
Asp Asp Leu Pro Ser His Glu Ala Pro Leu Ala Asp Ser Leu Glu Glu
                810                 815                 820

ctg gag cct cag cac atc tcc ctt tct gtt ttc ccc tca agt tct ctt      3151
Leu Glu Pro Gln His Ile Ser Leu Ser Val Phe Pro Ser Ser Ser Leu
            825                 830                 835

cac cca ctc acc ttc tcc tgt ggt gat aag ctg act ctg gat cag tta      3199
His Pro Leu Thr Phe Ser Cys Gly Asp Lys Leu Thr Leu Asp Gln Leu
        840                 845                 850

aag atg agg tgt gac tcc ctc atg ctc tga gtggtgaggc ttcaagcctt        3249
Lys Met Arg Cys Asp Ser Leu Met Leu
    855                 860

aaagtcagtg tgccctcaac cagcacagcc tgccccaatt cccccagccc ctgctccagc   3309

agctgtcatc tctgggtgcc accatcggtc tggctgcagc tagaggacag gcaagccagc   3369

tctgggggag tcttaggaac tgggagttgg tcttcactca gatgcctcat cttgcctttc   3429

ccagggcctt aaaattacat ccttcactgt gtggacctag agactccaac ttgaattcct   3489
```

```
agtaactttc ttggtatgct ggccagaaag ggaaatgagg aggagagtag aaaccacagc   3549

tcttagtagt aatggcatac agtctagagg accattcatg caatgactat ttctaaagca   3609

cctgctacac agcaggctgt acacagcaga tcagtactgt tcaacagaac ttcctgagat   3669

gatggaaatg ttctacctct gcactcactg tccagtacat tagacactag gcacattggc   3729

tgttaatcac ttggaatgtg tttagcttga ctgaggaatt aaattttgat tgtaaattta   3789

aatcgccaca catggctagt ggctactgta ttggagtgca cagctctaga tggctcctag   3849

attattgaga gccttcaaaa caaatcaacc tagttctata gatgaagaca taaaagacac   3909

tggtaaacac caaggtaaaa gggcccccaa ggtggtcatg actggtctca tttgcagaag   3969

tctaagaatg taccttttc tggccgggcg tggtagctca tgcctgtaat cccagcactt   4029

tgggaggctg a                                                        4040


<210> SEQ ID NO 5
<211> LENGTH: 2589
<212> TYPE: DNA
<213> ORGANISM: Homo Sapiens
<220> FEATURE:
<221> NAME/KEY: misc_feature
<222> LOCATION: (0)...(0)
<223> OTHER INFORMATION: coding sequence for IL12RB2
<220> FEATURE:
<221> NAME/KEY: CDS
<222> LOCATION: (1)...(2589)

<400> SEQUENCE: 5

atg gca cat act ttt aga gga tgc tca ttg gca ttt atg ttt ata atc       48
Met Ala His Thr Phe Arg Gly Cys Ser Leu Ala Phe Met Phe Ile Ile
 1               5                  10                  15

acg tgg ctg ttg att aaa gca aaa ata gat gcg tgc aag aga ggc gat       96
Thr Trp Leu Leu Ile Lys Ala Lys Ile Asp Ala Cys Lys Arg Gly Asp
            20                  25                  30

gtg act gtg aag cct tcc cat gta att tta ctt gga tcc act gtc aat      144
Val Thr Val Lys Pro Ser His Val Ile Leu Leu Gly Ser Thr Val Asn
        35                  40                  45

att aca tgc tct ttg aag ccc aga caa ggc tgc ttt cac tat tcc aga      192
Ile Thr Cys Ser Leu Lys Pro Arg Gln Gly Cys Phe His Tyr Ser Arg
    50                  55                  60

cgt aac aag tta atc ctg tac aag ttt gac aga aga atc aat ttt cac      240
Arg Asn Lys Leu Ile Leu Tyr Lys Phe Asp Arg Arg Ile Asn Phe His
 65                  70                  75                  80

cat ggc cac tcc ctc aat tct caa gtc aca ggt ctt ccc ctt ggt aca      288
His Gly His Ser Leu Asn Ser Gln Val Thr Gly Leu Pro Leu Gly Thr
                85                  90                  95

acc ttg ttt gtc tgc aaa ctg gcc tgt atc aat agt gat gaa att caa      336
Thr Leu Phe Val Cys Lys Leu Ala Cys Ile Asn Ser Asp Glu Ile Gln
            100                 105                 110

ata tgt gga gca gag atc ttc gtt ggt gtt gct cca gaa cag cct caa      384
Ile Cys Gly Ala Glu Ile Phe Val Gly Val Ala Pro Glu Gln Pro Gln
        115                 120                 125

aat tta tcc tgc ata cag aag gga gaa cag ggg act gtg gcc tgc acc      432
Asn Leu Ser Cys Ile Gln Lys Gly Glu Gln Gly Thr Val Ala Cys Thr
    130                 135                 140

tgg gaa aga gga cga gac acc cac tta tac act gag tat act cta cag      480
Trp Glu Arg Gly Arg Asp Thr His Leu Tyr Thr Glu Tyr Thr Leu Gln
145                 150                 155                 160

cta agt gga cca aaa aat tta acc tgg cag aag caa tgt aaa gac att      528
Leu Ser Gly Pro Lys Asn Leu Thr Trp Gln Lys Gln Cys Lys Asp Ile
                165                 170                 175
```

```
tat tgt gac tat ttg gac ttt gga atc aac ctc acc cct gaa tca cct      576
Tyr Cys Asp Tyr Leu Asp Phe Gly Ile Asn Leu Thr Pro Glu Ser Pro
            180                 185                 190

gaa tcc aat ttc aca gcc aag gtt act gct gtc aat agt ctt gga agc      624
Glu Ser Asn Phe Thr Ala Lys Val Thr Ala Val Asn Ser Leu Gly Ser
        195                 200                 205

tcc tct tca ctt cca tcc aca ttc aca ttc ttg gac ata gtg agg cct      672
Ser Ser Ser Leu Pro Ser Thr Phe Thr Phe Leu Asp Ile Val Arg Pro
    210                 215                 220

ctt cct ccg tgg gac att aga atc aaa ttt caa aag gct tct gtg agc      720
Leu Pro Pro Trp Asp Ile Arg Ile Lys Phe Gln Lys Ala Ser Val Ser
225                 230                 235                 240

aga tgt acc ctt tat tgg aga gat gag gga ctg gta ctg ctt aat cga      768
Arg Cys Thr Leu Tyr Trp Arg Asp Glu Gly Leu Val Leu Leu Asn Arg
                245                 250                 255

ctc aga tat cgg ccc agt aac agc agg ctc tgg aat atg gtt aat gtt      816
Leu Arg Tyr Arg Pro Ser Asn Ser Arg Leu Trp Asn Met Val Asn Val
            260                 265                 270

aca aag gcc aaa gga aga cat gat ttg ctg gat ctg aaa cca ttt aca      864
Thr Lys Ala Lys Gly Arg His Asp Leu Leu Asp Leu Lys Pro Phe Thr
        275                 280                 285

gaa tat gaa ttt cag att tcc tct aag cta cat ctt tat aag gga agt      912
Glu Tyr Glu Phe Gln Ile Ser Ser Lys Leu His Leu Tyr Lys Gly Ser
    290                 295                 300

tgg agt gat tgg agt gaa tca ttg aga gca caa aca cca gaa gaa gag      960
Trp Ser Asp Trp Ser Glu Ser Leu Arg Ala Gln Thr Pro Glu Glu Glu
305                 310                 315                 320

cct act ggg atg tta gat gtc tgg tac atg aaa cgg cac att gac tac     1008
Pro Thr Gly Met Leu Asp Val Trp Tyr Met Lys Arg His Ile Asp Tyr
                325                 330                 335

agt aga caa cag att tct ctt ttc tgg aag aat ctg agt gtc tca gag     1056
Ser Arg Gln Gln Ile Ser Leu Phe Trp Lys Asn Leu Ser Val Ser Glu
            340                 345                 350

gca aga gga aaa att ctc cac tat cag gtg acc ttg cag gag ctg aca     1104
Ala Arg Gly Lys Ile Leu His Tyr Gln Val Thr Leu Gln Glu Leu Thr
        355                 360                 365

gga ggg aaa gcc atg aca cag aac atc aca gga cac acc tcc tgg acc     1152
Gly Gly Lys Ala Met Thr Gln Asn Ile Thr Gly His Thr Ser Trp Thr
    370                 375                 380

aca gtc att cct aga acc gga aat tgg gct gtg gct gtg tct gca gca     1200
Thr Val Ile Pro Arg Thr Gly Asn Trp Ala Val Ala Val Ser Ala Ala
385                 390                 395                 400

aat tca aaa ggc agt tct ctg ccc act cgt att aac ata atg aac ctg     1248
Asn Ser Lys Gly Ser Ser Leu Pro Thr Arg Ile Asn Ile Met Asn Leu
                405                 410                 415

tgt gag gca ggg ttg ctg gct cct cgc cag gtc tct gca aac tca gag     1296
Cys Glu Ala Gly Leu Leu Ala Pro Arg Gln Val Ser Ala Asn Ser Glu
            420                 425                 430

ggc atg gac aac att ctg gtg act tgg cag cct ccc agg aaa gat ccc     1344
Gly Met Asp Asn Ile Leu Val Thr Trp Gln Pro Pro Arg Lys Asp Pro
        435                 440                 445

tct gct gtt cag gag tac gtg gtg gaa tgg aga gag ctc cat cca ggg     1392
Ser Ala Val Gln Glu Tyr Val Val Glu Trp Arg Glu Leu His Pro Gly
    450                 455                 460

ggt gac aca cag gtc cct cta aac tgg cta cgg agt cga ccc tac aat     1440
Gly Asp Thr Gln Val Pro Leu Asn Trp Leu Arg Ser Arg Pro Tyr Asn
465                 470                 475                 480

gtg tct gct ctg att tca gag aac ata aaa tcc tac atc tgt tat gaa     1488
Val Ser Ala Leu Ile Ser Glu Asn Ile Lys Ser Tyr Ile Cys Tyr Glu
                485                 490                 495
```

```
atc cgt gtg tat gca ctc tca ggg gat caa gga gga tgc agc tcc atc     1536
Ile Arg Val Tyr Ala Leu Ser Gly Asp Gln Gly Gly Cys Ser Ser Ile
            500                 505                 510

ctg ggt aac tct aag cac aaa gca cca ctg agt ggc ccc cac att aat     1584
Leu Gly Asn Ser Lys His Lys Ala Pro Leu Ser Gly Pro His Ile Asn
        515                 520                 525

gcc atc aca gag gaa aag ggg agc att tta att tca tgg aac agc att     1632
Ala Ile Thr Glu Glu Lys Gly Ser Ile Leu Ile Ser Trp Asn Ser Ile
    530                 535                 540

cca gtc cag gag caa atg ggc tgc ctc ctc cat tat agg ata tac tgg     1680
Pro Val Gln Glu Gln Met Gly Cys Leu Leu His Tyr Arg Ile Tyr Trp
545                 550                 555                 560

aag gaa cgg gac tcc aac tcc cag cct cag ctc tgt gaa att ccc tac     1728
Lys Glu Arg Asp Ser Asn Ser Gln Pro Gln Leu Cys Glu Ile Pro Tyr
                565                 570                 575

aga gtc tcc caa aat tca cat cca ata aac agc ctg cag ccc cga gtg     1776
Arg Val Ser Gln Asn Ser His Pro Ile Asn Ser Leu Gln Pro Arg Val
            580                 585                 590

aca tat gtc ctg tgg atg aca gct ctg aca gct gct ggt gaa agt tcc     1824
Thr Tyr Val Leu Trp Met Thr Ala Leu Thr Ala Ala Gly Glu Ser Ser
        595                 600                 605

cac gga aat gag agg gaa ttt tgt ctg caa ggt aaa gcc aat tgg atg     1872
His Gly Asn Glu Arg Glu Phe Cys Leu Gln Gly Lys Ala Asn Trp Met
    610                 615                 620

gcg ttt gtg gca cca agc att tgc att gct atc atc atg gtg ggc att     1920
Ala Phe Val Ala Pro Ser Ile Cys Ile Ala Ile Ile Met Val Gly Ile
625                 630                 635                 640

ttc tca acg cat tac ttc cag caa aag gtg ttt gtt ctc cta gca gcc     1968
Phe Ser Thr His Tyr Phe Gln Gln Lys Val Phe Val Leu Leu Ala Ala
                645                 650                 655

ctc aga cct cag tgg tgt agc aga gaa att cca gat cca gca aat agc     2016
Leu Arg Pro Gln Trp Cys Ser Arg Glu Ile Pro Asp Pro Ala Asn Ser
            660                 665                 670

act tgc gct aag aaa tat ccc att gca gag gag aag aca cag ctg ccc     2064
Thr Cys Ala Lys Lys Tyr Pro Ile Ala Glu Glu Lys Thr Gln Leu Pro
        675                 680                 685

ttg gac agg ctc ctg ata gac tgg ccc acg cct gaa gat cct gaa ccg     2112
Leu Asp Arg Leu Leu Ile Asp Trp Pro Thr Pro Glu Asp Pro Glu Pro
    690                 695                 700

ctg gtc atc agt gaa gtc ctt cat caa gtg acc cca gtt ttc aga cat     2160
Leu Val Ile Ser Glu Val Leu His Gln Val Thr Pro Val Phe Arg His
705                 710                 715                 720

ccc ccc tgc tcc aac tgg cca caa agg gaa aaa gga atc caa ggt cat     2208
Pro Pro Cys Ser Asn Trp Pro Gln Arg Glu Lys Gly Ile Gln Gly His
                725                 730                 735

cag gcc tct gag aaa gac atg atg cac agt gcc tca agc cca cca cct     2256
Gln Ala Ser Glu Lys Asp Met Met His Ser Ala Ser Ser Pro Pro Pro
            740                 745                 750

cca aga gct ctc caa gct gag agc aga caa ctg gtg gat ctg tac aag     2304
Pro Arg Ala Leu Gln Ala Glu Ser Arg Gln Leu Val Asp Leu Tyr Lys
        755                 760                 765

gtg ctg gag agc agg ggc tcc gac cca aag ccc gaa aac cca gcc tgt     2352
Val Leu Glu Ser Arg Gly Ser Asp Pro Lys Pro Glu Asn Pro Ala Cys
    770                 775                 780

ccc tgg acg gtg ctc cca gca ggt gac ctt ccc acc cat gat ggc tac     2400
Pro Trp Thr Val Leu Pro Ala Gly Asp Leu Pro Thr His Asp Gly Tyr
785                 790                 795                 800

tta ccc tcc aac ata gat gac ctc ccc tca cat gag gca cct ctc gct     2448
Leu Pro Ser Asn Ile Asp Asp Leu Pro Ser His Glu Ala Pro Leu Ala
                805                 810                 815
```

-continued

```
gac tct ctg gaa gaa ctg gag cct cag cac atc tcc ctt tct gtt ttc      2496
Asp Ser Leu Glu Glu Leu Glu Pro Gln His Ile Ser Leu Ser Val Phe
            820                 825                 830

ccc tca agt tct ctt cac cca ctc acc ttc tcc tgt ggt gat aag ctg      2544
Pro Ser Ser Ser Leu His Pro Leu Thr Phe Ser Cys Gly Asp Lys Leu
        835                 840                 845

act ctg gat cag tta aag atg agg tgt gac tcc ctc atg ctc tga          2589
Thr Leu Asp Gln Leu Lys Met Arg Cys Asp Ser Leu Met Leu
    850                 855                 860


<210> SEQ ID NO 6
<211> LENGTH: 862
<212> TYPE: PRT
<213> ORGANISM: Homo sapiens

<400> SEQUENCE: 6

Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
            20                  25                  30

Val Thr Val Lys Pro Ser His Val Ile Leu Leu Gly Ser Thr Val Asn
        35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
            100                 105                 110

Ile Cys Gly Ala Glu Ile Phe Val Gly Val Ala Pro Glu Gln Pro Gln
        115                 120                 125

Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
        195                 200                 205

Ser Ser Ser Leu Pro Ser Thr Phe Thr Phe Leu Asp Ile Val Arg Pro
    210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
        275                 280                 285

Glu Tyr Glu Phe Gln Ile Ser Ser Lys Leu His Leu Tyr Lys Gly Ser
    290                 295                 300

Trp Ser Asp Trp Ser Glu Ser Leu Arg Ala Gln Thr Pro Glu Glu Glu
305                 310                 315                 320
```

-continued

```
Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
        355                 360                 365

Gly Gly Lys Ala Met Thr Gln Asn Ile Thr Gly His Thr Ser Trp Thr
    370                 375                 380

Thr Val Ile Pro Arg Thr Gly Asn Trp Ala Val Ala Val Ser Ala Ala
385                 390                 395                 400

Asn Ser Lys Gly Ser Ser Leu Pro Thr Arg Ile Asn Ile Met Asn Leu
                405                 410                 415

Cys Glu Ala Gly Leu Leu Ala Pro Arg Gln Val Ser Ala Asn Ser Glu
            420                 425                 430

Gly Met Asp Asn Ile Leu Val Thr Trp Gln Pro Pro Arg Lys Asp Pro
        435                 440                 445

Ser Ala Val Gln Glu Tyr Val Val Glu Trp Arg Glu Leu His Pro Gly
    450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
                485                 490                 495

Ile Arg Val Tyr Ala Leu Ser Gly Asp Gln Gly Gly Cys Ser Ser Ile
            500                 505                 510

Leu Gly Asn Ser Lys His Lys Ala Pro Leu Ser Gly Pro His Ile Asn
        515                 520                 525

Ala Ile Thr Glu Glu Lys Gly Ser Ile Leu Ile Ser Trp Asn Ser Ile
    530                 535                 540

Pro Val Gln Glu Gln Met Gly Cys Leu Leu His Tyr Arg Ile Tyr Trp
545                 550                 555                 560

Lys Glu Arg Asp Ser Asn Ser Gln Pro Gln Leu Cys Glu Ile Pro Tyr
                565                 570                 575

Arg Val Ser Gln Asn Ser His Pro Ile Asn Ser Leu Gln Pro Arg Val
            580                 585                 590

Thr Tyr Val Leu Trp Met Thr Ala Leu Thr Ala Ala Gly Glu Ser Ser
        595                 600                 605

His Gly Asn Glu Arg Glu Phe Cys Leu Gln Gly Lys Ala Asn Trp Met
    610                 615                 620

Ala Phe Val Ala Pro Ser Ile Cys Ile Ala Ile Ile Met Val Gly Ile
625                 630                 635                 640

Phe Ser Thr His Tyr Phe Gln Gln Lys Val Phe Val Leu Leu Ala Ala
                645                 650                 655

Leu Arg Pro Gln Trp Cys Ser Arg Glu Ile Pro Asp Pro Ala Asn Ser
            660                 665                 670

Thr Cys Ala Lys Lys Tyr Pro Ile Ala Glu Glu Lys Thr Gln Leu Pro
        675                 680                 685

Leu Asp Arg Leu Leu Ile Asp Trp Pro Thr Pro Glu Asp Pro Glu Pro
    690                 695                 700

Leu Val Ile Ser Glu Val Leu His Gln Val Thr Pro Val Phe Arg His
705                 710                 715                 720

Pro Pro Cys Ser Asn Trp Pro Gln Arg Glu Lys Gly Ile Gln Gly His
                725                 730                 735
```

-continued

```
Gln Ala Ser Glu Lys Asp Met Met His Ser Ala Ser Ser Pro Pro Pro
            740                 745                 750

Pro Arg Ala Leu Gln Ala Glu Ser Arg Gln Leu Val Asp Leu Tyr Lys
        755                 760                 765

Val Leu Glu Ser Arg Gly Ser Asp Pro Lys Pro Glu Asn Pro Ala Cys
    770                 775                 780

Pro Trp Thr Val Leu Pro Ala Gly Asp Leu Pro Thr His Asp Gly Tyr
785                 790                 795                 800

Leu Pro Ser Asn Ile Asp Asp Leu Pro Ser His Glu Ala Pro Leu Ala
                805                 810                 815

Asp Ser Leu Glu Glu Leu Glu Pro Gln His Ile Ser Leu Ser Val Phe
            820                 825                 830

Pro Ser Ser Ser Leu His Pro Leu Thr Phe Ser Cys Gly Asp Lys Leu
        835                 840                 845

Thr Leu Asp Gln Leu Lys Met Arg Cys Asp Ser Leu Met Leu
    850                 855                 860
```